(12) United States Patent
Gupta et al.

(10) Patent No.: US 9,777,286 B2
(45) Date of Patent: Oct. 3, 2017

(54) ZEA MAYS METALLOTHIONEIN-LIKE REGULATORY ELEMENTS AND USES THEREOF

(71) Applicant: Dow AgroSciences LLC, Indianapolis, IN (US)

(72) Inventors: Manju Gupta, Carmel, IN (US); Sandeep Kumar, Carmel, IN (US); Navin Elango, Indianapolis, IN (US); Karthik Narayna Muthuraman, Boston, MA (US); Jeffrey Beringer, Carmel, IN (US); Huixia Wu, Zionsville, IN (US); Nagesh Sardesai, West Lafayette, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 57 days.

(21) Appl. No.: 14/505,055

(22) Filed: Oct. 2, 2014

(65) Prior Publication Data
US 2015/0101083 A1   Apr. 9, 2015

Related U.S. Application Data

(60) Provisional application No. 61/886,943, filed on Oct. 4, 2013.

(51) Int. Cl.
*C12N 15/82* (2006.01)

(52) U.S. Cl.
CPC ..... *C12N 15/8227* (2013.01); *C12N 15/8216* (2013.01); *C12N 15/8222* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 5,004,863 A | 4/1991 | Umbeck |
| 5,015,580 A | 5/1991 | Christou et al. |
| 5,159,135 A | 10/1992 | Umbeck et al. |
| 5,188,960 A | 2/1993 | Payne et al. |
| 5,302,523 A | 4/1994 | Coffee et al. |
| 5,380,831 A | 1/1995 | Adang et al. |
| 5,384,253 A | 1/1995 | Krzyzek et al. |
| 5,464,765 A | 11/1995 | Coffee et al. |
| 5,508,184 A | 4/1996 | Negrutiu et al. |
| 5,538,880 A | 7/1996 | Lundquist et al. |
| 5,550,318 A | 8/1996 | Adams et al. |
| 5,591,616 A | 1/1997 | Hiei et al. |
| 5,635,055 A | 6/1997 | Sweet et al. |
| 5,691,308 A | 11/1997 | Payne et al. |
| 5,710,020 A | 1/1998 | Adang |
| 5,750,871 A | 5/1998 | Moloney et al. |
| 5,824,877 A | 10/1998 | Hinchee et al. |
| 5,846,797 A | 12/1998 | Strickland |
| 5,981,840 A | 11/1999 | Zhao et al. |
| 6,083,499 A | 7/2000 | Narva et al. |
| 6,096,708 A | 8/2000 | Payne et al. |
| 6,114,138 A | 9/2000 | Adang |
| 6,127,180 A | 10/2000 | Narva et al. |
| 6,160,208 A | 12/2000 | Lundquist et al. |
| 6,166,302 A | 12/2000 | Merlo et al. |
| 6,251,656 B1 | 6/2001 | Adang |
| 6,340,593 B1 | 1/2002 | Cardineau et al. |
| 6,384,301 B1 | 5/2002 | Martinell et al. |
| 6,399,861 B1 | 6/2002 | Anderson et al. |
| 6,403,865 B1 | 6/2002 | Koziel et al. |
| 6,548,291 B1 | 4/2003 | Narva et al. |
| 6,573,240 B1 | 6/2003 | Payne et al. |
| 6,624,145 B1 | 9/2003 | Narva et al. |
| 6,624,344 B1 | 9/2003 | Rangan et al. |
| 6,774,282 B1 * | 8/2004 | Ritchie ................ C07K 14/825 435/320.1 |
| 7,060,876 B2 | 6/2006 | Hiei et al. |
| 7,179,902 B2 | 2/2007 | Cowen et al. |
| 7,214,854 B2 * | 5/2007 | Diehn ................ C12N 15/8227 435/320.1 |
| 7,214,855 B2 * | 5/2007 | Diehn ................ C12N 15/8227 435/320.1 |
| 7,838,733 B2 | 11/2010 | Wright et al. |
| 8,283,522 B2 | 10/2012 | Wright et al. |
| 2009/0093366 A1 | 4/2009 | Wright et al. |
| 2009/0104700 A1 | 4/2009 | Samuel et al. |
| 2011/0107455 A1 | 5/2011 | Lira et al. |
| 2013/0157369 A1 | 6/2013 | Miller |
| 2013/0232647 A1 | 9/2013 | Brown |

FOREIGN PATENT DOCUMENTS

| | | |
|---|---|---|
| WO | 95/06722 A1 | 3/1995 |
| WO | 9713402 A1 | 4/1997 |
| WO | 00/53763 | 9/2000 |

(Continued)

OTHER PUBLICATIONS

Potenza et al., In Vitro Cell Dev Biol Plant 40:1-22 (2004).*
Saha et al., In Silico Biol 7(1):7-19 (2007).*
Vaughn et al., RNA 18:368-84 (2012).*
Donald & Cashmore, EMBO J 9:1717-26 (1990).*
Kim et al., Plant Mol Biol 24:105-17 (1994).*
Dolferus et al., Plant Physiol 105:1075-87 (1994).*
Loke et al., Plant Physiol 138:1457-68 (2005).*
Mizusawa et al., Nucl Acid Res 14(3):1319-24 (1986).*
Loke J., et al., (2005) Plant Physiology 138(3): 1457-1468.

(Continued)

*Primary Examiner* — Amjad Abraham
*Assistant Examiner* — Russell Boggs
(74) *Attorney, Agent, or Firm* — Eric J. Kraus; Barnes & Thornburg LLP

(57) ABSTRACT

Provided are constructs and methods for expressing a transgene in plant cells and/or plant tissues using *Zea mays* metallothionein-like gene regulatory elements.

28 Claims, 12 Drawing Sheets

(56) References Cited

FOREIGN PATENT DOCUMENTS

| WO | 2005/063998 | | 7/2005 |
|---|---|---|---|
| WO | 2005107437 | A2 | 11/2005 |
| WO | 2011146524 | A1 | 11/2011 |
| WO | 2012016222 | A2 | 2/2012 |
| WO | 2013016546 | A2 | 1/2013 |
| WO | 2013116700 | A1 | 8/2013 |

OTHER PUBLICATIONS

Sambrook et al. (ed.), Molecular Cloning: A Laboratory Manual, 2nd ed., vol. 1-3, Cold Spring Harbor Laboratory Press, Cold Spring Harbor, New York, 1989. [Book reference submitted upon request].
Mullis et al., Cold Spring Harbor Symp. Quant. Biol., 51:263 (1987).
Erlich, ed., PCR Technology, (Stockton Press, NY, 1989). [Book reference submitted upon request].
Smith and Waterman (1981) Adv. Math. 2:482.
Needleman and Wunsch (1970) J. Mol. Biol. 48:443.
Pearson and Lipman (1988) Proc. Natl. Acad. Sc. U.S.A. 85:2444.
Higgins and Sharp (1988) Gene 73:237-44.
Higgins and Sharp (1989) Cabios 5:151-3.
Corpet et al., (1988) Nucleic Acids Res. 16:10881-90.
Huang et al., (1992) Comp. Appl. Biosci. 8:155-65.
Pearson et al. (1994) Methods Mol. Biol. 24:307-31.
Tatiana et al., (1999) FEMS Microbial. Lett. 174-247-50.
Blast (tm); Altschul et al. (1990)1 Mol. Biol. 215:403-10.
Mueller et al. (1978) Cell 15:579-85.
Klein et al., (1987) Nature 327:70-73.
Chung et al., (2006) Trends Plant Sci. 11(1):1-4.
Rios et al., (2002) Plant J. 32:243-53.
Goto-Fumiyuki et al., Nature Biotech 17:282-286 (1999).
Miki et al., Methods in Plant Molecular Biology and Biotechnology, Glick, B.R. and Thompson, J.E. Eds., CRC Press, Inc., Boca Raton, pp. 67-88 (1993). [Book reference submitted upon request].
Gruber et al., Methods in Plant Molecular Biology and Biotechnology, Glick, B.R. and Thompson, J.E. Eds., CRC Press, Inc., Boca Raton, pp. 89-119 (1993). [Book reference submitted upon request].
Maize database available at www.maizegdb.org.
Wang et al., (2009): "Genome-Wide and Organ-Specific Landscapes of Epigenetic Modifications and Their Relationships to mRNA and Small RNA Transcriptomes in Maize," Plant Cell 21:1053-1069.
Alexandrove N., et al., (2009) "Insights into corn genes derived from large-scale cDNA sequencing," Plant Molecular Biology 69:179-194.
Christensen et al., (1992) Plant Molecular Biology 18:675-689.
Shagin et al., (2004) Mol Biol Evol 21:841-50.
An et al., (1989) Plant Cell 1:115-22.
Ishida Y. et (1996) "High efficiency transformation of maize (Zea mays L.) mediated by Agrobacterium tumefaciens,"Nature Biotechnol 14:745-750.
Frame et al., (2006) "Improved Agrobacterium-mediated transformation of three maize inbred lines using MS salts," Plant Cell Rep 25:1024-1034.
Gelvin, S., 2006, Agrobacterium Virulence Gene Induction, in Wang, K., ed., Agrobacterium Protocols Second Edition vol. 1, Humana Press, p. 79. [Book reference submitted upon request].
International Search Report and Written Opinion, International Application No. PCT/US2014/058753, Dec. 30, 2014, 17 pages.
Maize Genome Constortium, Zea mays Chromosome 1 Clone ZMMBBb-400N15, Sep. 21, 2013, available at http://www.ncbi.nlm.nih.gov/nuccore/AC217311.4.
Wilson, R. et al., "Zea mays chromosome 1 clone CH201-310B22," Sep. 21, 2013, available at http://www.ncbi.nlm.nih.gov/nuccore/AC217938.
Chan, A. et al., "Zea mays Strain B73 clone ZMMBBb0152E04," Jan. 25, 2005, available at http://www.ncbi.nlm.nih.gov/nuccore/ac155387.
GenBank Accession AC217311, Zea mays cultivar B73 chromosome 1 clone ZMMBBb-400N15, Sep. 21, 2013, available online at https://www.ncbi.nlm.nih.gov/nuccore/AC217311, accessed Dec. 15, 2016, 30 pages.
Extended European Search Report, European Application No. 14850603.3—1410/3052633, dated Mar. 2, 2017, 7 pages.
Framond, A., "Metallothionein-Like Gene from Maize (Zea Mays) Cloning and Characterization", FEBS Letters, Elsevier, Amsterdam, NL, vol. 290, No. 1/02, Jan. 1, 1991.

* cited by examiner

Fig. 6A

| | | 1 30 |
|---|---|---|
| SEQ ID NO:2 Truncated Promoter | (1) | ------------------------------ |
| SEQ ID NO:1 Full Length Promoter | (1) | ACCATATCATGTCTCAAGCCTTAATACACT |
| | | 31 60 |
| SEQ ID NO:2 Truncated Promoter | (1) | ------------------------------ |
| SEQ ID NO:1 Full Length Promoter | (31) | TTTAAATAAATTTAAATCATTTAATAGAAA |
| | | 61 90 |
| SEQ ID NO:2 Truncated Promoter | (1) | ------------------------------ |
| SEQ ID NO:1 Full Length Promoter | (61) | CTAATTACATGTTAATACATCACTATAAAA |
| | | 91 120 |
| SEQ ID NO:2 Truncated Promoter | (1) | -------------------------TTTAA |
| SEQ ID NO:1 Full Length Promoter | (91) | AAAATTAATGGTTGCACCGTAAAGCTTTAA |
| | | 121 150 |
| SEQ ID NO:2 Truncated Promoter | (6) | CTTGTGCATCTATACTCTAATAGTTTGTGG |
| SEQ ID NO:1 Full Length Promoter | (121) | CTTGTGCATCTATACTCTAATAGTTTGTGG |
| | | 151 180 |
| SEQ ID NO:2 Truncated Promoter | (36) | TCCAACGCCTCGGTCCGACATCTATAGAAG |
| SEQ ID NO:1 Full Length Promoter | (151) | TCCAACGCCTCGGTCCGACATCTATAGAAG |
| | | 181 210 |
| SEQ ID NO:2 Truncated Promoter | (66) | TCTTTTTTTCTTTATTATTTGGTTTCTTTG |
| SEQ ID NO:1 Full Length Promoter | (181) | TCTTTTTTTCTTTATTATTTGGTTTCTTTG |
| | | 211 240 |
| SEQ ID NO:2 Truncated Promoter | (96) | TGAGCTTCACGTTCAGTTTGGCCCTATTTG |
| SEQ ID NO:1 Full Length Promoter | (211) | TGAGCTTCACGTTCAGTTTGGCCCTATTTG |
| | | 241 270 |
| SEQ ID NO:2 Truncated Promoter | (126) | TACTCTTGCATATACTTATAGATATGTAAC |
| SEQ ID NO:1 Full Length Promoter | (241) | TACTCTTGCATATACTTATAGATATGTAAC |
| | | 271 300 |
| SEQ ID NO:2 Truncated Promoter | (156) | ATGTTTTCTAACATCTTGCTTGAGATGTTA |
| SEQ ID NO:1 Full Length Promoter | (271) | ATGTTTTCTAACATCTTGCTTGAGATGTTA |
| | | 301 330 |
| SEQ ID NO:2 Truncated Promoter | (186) | TTCATTCGAAGCATCCCTTTGTCTAAGTCC |
| SEQ ID NO:1 Full Length Promoter | (301) | TTCATTCGAAGCATCCCTTTGTCTAAGTCC |
| | | 331 360 |
| SEQ ID NO:2 Truncated Promoter | (216) | ACTTGTGCACCCTTTGA-------------- |
| SEQ ID NO:1 Full Length Promoter | (331) | ACTTGTGCACCCTTTGAAAAAATGTTAGCA |
| | | 361 390 |
| SEQ ID NO:2 Truncated Promoter | (233) | ------------------------------ |
| SEQ ID NO:1 Full Length Promoter | (361) | TAAATGATTGTGTTAACCATCAAAACACCA |
| | | 391 420 |
| SEQ ID NO:2 Truncated Promoter | (233) | ------------------------------ |
| SEQ ID NO:1 Full Length Promoter | (391) | AAACTTATTTTAAACGGACCTAAGTCTAT |
| | | 421 450 |
| SEQ ID NO:2 Truncated Promoter | (233) | --------------GCTAGCATGAGGAACA |
| SEQ ID NO:1 Full Length Promoter | (421) | TTTACTTGCAATGAGCTAGCATGAGGAACA |
| | | 451 480 |
| SEQ ID NO:2 Truncated Promoter | (249) | TGGAGCAACATTAAACTCGAAACAGGAGGC |
| SEQ ID NO:1 Full Length Promoter | (451) | TGGAGCAACATTAAACTCGAAACAGGAGGC |
| | | 481 510 |
| SEQ ID NO:2 Truncated Promoter | (279) | AGTATCAAAT-------------------- |
| SEQ ID NO:1 Full Length Promoter | (481) | AGTATCAAATACTCCCTCTGTTTCTTTTTA |
| | | 511 540 |
| SEQ ID NO:2 Truncated Promoter | (289) | ------------------------------ |
| SEQ ID NO:1 Full Length Promoter | (511) | TTAGTCGCTGGATAGTGAAATTTTGCACTA |

Fig. 6B

```
                                        541                         570
SEQ ID NO:2 Truncated Promoter   (289)  ------------------------------
SEQ ID NO:1 Full Length Promoter (541)  TCCAGCGACTAATAAAAGAAACGGAGGGA
                                        571                         600
SEQ ID NO:2 Truncated Promoter   (289)  ----GAGAGTCGATCTTAAGAACATGACGT
SEQ ID NO:1 Full Length Promoter (571)  GTATGAGAGTCGATCTTAAGAACATGACGT
                                        601                         630
SEQ ID NO:2 Truncated Promoter   (315)  ATGATCCATACCCTCAAATCTGTTTGAGAA
SEQ ID NO:1 Full Length Promoter (601)  ATGATCCATACCCTCAAATCTGTTTGAGAA
                                        631                         660
SEQ ID NO:2 Truncated Promoter   (345)  AAATCACTATCGAAGGAGGCTACTTGTTTT
SEQ ID NO:1 Full Length Promoter (631)  AAATCACTATCGAAGGAGGCTACTTGTTTT
                                        661                         690
SEQ ID NO:2 Truncated Promoter   (375)  CTTCTTTGCGTAGAAGATAA----------
SEQ ID NO:1 Full Length Promoter (661)  CTTCTTTGCGTAGAAGATAATACTCCTCCT
                                        691                         720
SEQ ID NO:2 Truncated Promoter   (395)  ------------------------------
SEQ ID NO:1 Full Length Promoter (691)  GTCCTAAATTAATATTTGTTTAAACTTTTT
                                        721                         750
SEQ ID NO:2 Truncated Promoter   (395)  ------------------------------
SEQ ID NO:1 Full Length Promoter (721)  ACTAAATTCATGTAATAATTAATGTATGCG
                                        751                         780
SEQ ID NO:2 Truncated Promoter   (395)  ------------------------------
SEQ ID NO:1 Full Length Promoter (751)  TTATATATATATGTCTAGGTTTATAATTAT
                                        781                         810
SEQ ID NO:2 Truncated Promoter   (395)  ------------------------------
SEQ ID NO:1 Full Length Promoter (781)  TCATATGAATATGAACATAAAAATCTAGGG
                                        811                         840
SEQ ID NO:2 Truncated Promoter   (395)  ------------------------------
SEQ ID NO:1 Full Length Promoter (811)  CTAAAACGACTACTATTTGAAAACGGAAG
                                        841                         870
SEQ ID NO:2 Truncated Promoter   (395)  -----GTAAGTTATTTAAGCGGAGGGGAAC
SEQ ID NO:1 Full Length Promoter (841)  GAGTAGTAAGTTATTTAAGCGGAGGGGAAC
                                        871                         900
SEQ ID NO:2 Truncated Promoter   (420)  CATGATGGGCTAGTGATTTAATTTACATAT
SEQ ID NO:1 Full Length Promoter (871)  CATGATGGGCTAGTGATTTAATTTACATAT
                                        901                         930
SEQ ID NO:2 Truncated Promoter   (450)  ATATATTGGTGTTCTGGGCTCTTACATGAG
SEQ ID NO:1 Full Length Promoter (901)  ATATATTGGTGTTCTGGGCTCTTACATGAG
                                        931                         960
SEQ ID NO:2 Truncated Promoter   (480)  AAGATCTAGTTAACTGTTGTTACTGAACAG
SEQ ID NO:1 Full Length Promoter (931)  AAGATCTAGTTAACTGTTGTTACTGAACAG
                                        961                         990
SEQ ID NO:2 Truncated Promoter   (510)  CGAAGACAAATATATAATTTAAGCTCCCCA
SEQ ID NO:1 Full Length Promoter (961)  CGAAGACAAATATATAATTTAAGCTCCCCA
                                        991                        1020
SEQ ID NO:2 Truncated Promoter   (540)  ACTGCTAGTGATTCTGTTAAGAGGTAATGT
SEQ ID NO:1 Full Length Promoter (991)  ACTGCTAGTGATTCTGTTAAGAGGTAATGT
                                       1021                        1050
SEQ ID NO:2 Truncated Promoter   (570)  TTAAAGTAAATT------------------
SEQ ID NO:1 Full Length Promoter (1021) TTAAAGTAAATTACAAGAGCCCGTCTAGC
                                       1051                        1080
SEQ ID NO:2 Truncated Promoter   (582)  ------------------------------
SEQ ID NO:1 Full Length Promoter (1051) TCAGTCGGTAGAGCGCAAGGCTCTTAACCT
```

Fig. 6C

```
                                           1081                      1110
SEQ ID NO:2 Truncated Promoter    (582)  ------------------------------
SEQ ID NO:1 Full Length Promoter  (1081) TGTGGTCGTGGGTTCGAGCCCCACGGTGGG
                                           1111                      1140
SEQ ID NO:2 Truncated Promoter    (582)  ------------------------------
SEQ ID NO:1 Full Length Promoter  (1111) CGCACAATTTTTTGTTTTTTGACATTTTTT
                                           1141                      1170
SEQ ID NO:2 Truncated Promoter    (582)  ----GCTTAGTTGCAGACGGTTTTTCCCCT
SEQ ID NO:1 Full Length Promoter  (1141) GTTTGCTTAGTTGCAGACGGTTTTTCCCCT
                                           1171                      1200
SEQ ID NO:2 Truncated Promoter    (608)  GCTAGGAGATTTCCGAGAGAAAAAAAAGGC
SEQ ID NO:1 Full Length Promoter  (1171) GCTAGGAGATTTCCGAGAGAAAAAAAAGGC
                                           1201                      1230
SEQ ID NO:2 Truncated Promoter    (638)  ACTACAGGTTAACCAAAACCACCAACCTTT
SEQ ID NO:1 Full Length Promoter  (1201) ACTACAGGTTAACCAAAACCACCAACCTTT
                                           1231                      1260
SEQ ID NO:2 Truncated Promoter    (668)  GGAGCGTCGAGGCGACGGGCATTTGCGTAG
SEQ ID NO:1 Full Length Promoter  (1231) GGAGCGTCGAGGCGACGGGCATTTGCGTAG
                                           1261                      1290
SEQ ID NO:2 Truncated Promoter    (698)  TTGAAGCTTACAAAGTTGCATATGAGATGA
SEQ ID NO:1 Full Length Promoter  (1261) TTGAAGCTTACAAAGTTGCATATGAGATGA
                                           1291                      1320
SEQ ID NO:2 Truncated Promoter    (728)  GTGCCGGACATGAAGCGGATAACGTTTTAA
SEQ ID NO:1 Full Length Promoter  (1291) GTGCCGGACATGAAGCGGATAACGTTTTAA
                                           1321                      1350
SEQ ID NO:2 Truncated Promoter    (758)  ACTGGCAACAATATCTAGCTGTTTCAAATT
SEQ ID NO:1 Full Length Promoter  (1321) ACTGGCAACAATATCTAGCTGTTTCAAATT
                                           1351                      1380
SEQ ID NO:2 Truncated Promoter    (788)  CAGGCGTGGGAAGCTACGCCTACGCGCCCT
SEQ ID NO:1 Full Length Promoter  (1351) CAGGCGTGGGAAGCTACGCCTACGCGCCCT
                                           1381                      1410
SEQ ID NO:2 Truncated Promoter    (818)  GGACGGCGTGTAAAGAGCCAGCATCGGCAT
SEQ ID NO:1 Full Length Promoter  (1381) GGACGGCGTGTAAAGAGCCAGCATCGGCAT
                                           1411                      1440
SEQ ID NO:2 Truncated Promoter    (848)  CATTGTCAAACGATCGACAAGGCCAAGAAA
SEQ ID NO:1 Full Length Promoter  (1411) CATTGTCAAACGATCGACAAGGCCAAGAAA
                                           1441                      1470
SEQ ID NO:2 Truncated Promoter    (878)  TTCCAAATATATTATTAATAAAAAAGAAGG
SEQ ID NO:1 Full Length Promoter  (1441) TTCCAAATATATTATTAATAAAAAAGAAGG
                                           1471                      1500
SEQ ID NO:2 Truncated Promoter    (908)  CACAAATTAGTTTGGTTTTTTAGTATGTGT
SEQ ID NO:1 Full Length Promoter  (1471) CACAAATTAGTTTGGTTTTTTAGTATGTGT
                                           1501                      1530
SEQ ID NO:2 Truncated Promoter    (938)  GGCGGAGGAAATTTTGAGAACGAACGTATC
SEQ ID NO:1 Full Length Promoter  (1501) GGCGGAGGAAATTTTGAGAACGAACGTATC
                                           1531                      1560
SEQ ID NO:2 Truncated Promoter    (968)  AAAGAAGGCACAAGACGATATAGATTGACG
SEQ ID NO:1 Full Length Promoter  (1531) AAAGAAGGCACAAGACGATATAGATTGACG
                                           1561                      1590
SEQ ID NO:2 Truncated Promoter    (998)  CGGCTAGAAGTTGCAGCAAGACAGTGGGTA
SEQ ID NO:1 Full Length Promoter  (1561) CGGCTAGAAGTTGCAGCAAGACAGTGGGTA
                                           1591                      1620
SEQ ID NO:2 Truncated Promoter    (1028) CGGTCTTATATATCCTAATAAATAAAAAAT
SEQ ID NO:1 Full Length Promoter  (1591) CGGTCTTATATATCCTAATAAATAAAAAAT
```

Fig. 6D

```
                                          1621                           1650
SEQ ID NO:2 Truncated Promoter   (1058)   AAAACTATAGTGTGTCAAATGTCAACAAGA
SEQ ID NO:1 Full Length Promoter (1621)   AAAACTATAGTGTGTCAAATGTCAACAAGA
                                          1651                           1680
SEQ ID NO:2 Truncated Promoter   (1088)   GGAGGAGGCAGCCAAATTAGCAGAGGGAGA
SEQ ID NO:1 Full Length Promoter (1651)   GGAGGAGGCAGCCAAATTAGCAGAGGGAGA
                                          1681                           1710
SEQ ID NO:2 Truncated Promoter   (1118)   CAAGTAGAGCACGCCTTATTAGCTTGCTTA
SEQ ID NO:1 Full Length Promoter (1681)   CAAGTAGAGCACGCCTTATTAGCTTGCTTA
                                          1711                           1740
SEQ ID NO:2 Truncated Promoter   (1148)   TTTATCGTGGTGGTGTACTTGTTAATTACT
SEQ ID NO:1 Full Length Promoter (1711)   TTTATCGTGGTGGTGTACTTGTTAATTACT
                                          1741                           1770
SEQ ID NO:2 Truncated Promoter   (1178)   GGCACGCATTATCAACAACGCAGTTCTGGA
SEQ ID NO:1 Full Length Promoter (1741)   GGCACGCATTATCAACAACGCAGTTCTGGA
                                          1771                           1800
SEQ ID NO:2 Truncated Promoter   (1208)   TGTGAATCTAGACAAACATTTGTCTAGGTT
SEQ ID NO:1 Full Length Promoter (1771)   TGTGAATCTAGACAAACATTTGTCTAGGTT
                                          1801                           1830
SEQ ID NO:2 Truncated Promoter   (1238)   CCGCACGTATAGTTTTTTTTCTTTTTTTTT
SEQ ID NO:1 Full Length Promoter (1801)   CCGCACGTATAGTTTTTTTTCTTTTTTTTT
                                          1831                           1860
SEQ ID NO:2 Truncated Promoter   (1268)   TGGGGGGGGGGTGGGGGGGGGGGGGAACGG
SEQ ID NO:1 Full Length Promoter (1831)   TGGGGGGGGGGTGGGGGGGGGGGGGAACGG
                                          1861                           1890
SEQ ID NO:2 Truncated Promoter   (1298)   AAGCTGTAATAAACGGTACTAGGAACGAAA
SEQ ID NO:1 Full Length Promoter (1861)   AAGCTGTAATAAACGGTACTAGGAACGAAA
                                          1891                           1920
SEQ ID NO:2 Truncated Promoter   (1328)   GCAACCGCCGCGCGCATGTTTTTGCAATAG
SEQ ID NO:1 Full Length Promoter (1891)   GCAACCGCCGCGCGCATGTTTTTGCAATAG
                                          1921                           1950
SEQ ID NO:2 Truncated Promoter   (1358)   ATTACGGTGACCTTGATGCACCACCGCGTG
SEQ ID NO:1 Full Length Promoter (1921)   ATTACGGTGACCTTGATGCACCACCGCGTG
                                          1951                           1980
SEQ ID NO:2 Truncated Promoter   (1388)   CTATAAAAACCAGTGTCCCCGAGTCTACTC
SEQ ID NO:1 Full Length Promoter (1951)   CTATAAAAACCAGTGTCCCCGAGTCTACTC
                                          1981                           2010
SEQ ID NO:2 Truncated Promoter   (1418)   ATCAACCAATCCATAACTCGAAACCTTTTC
SEQ ID NO:1 Full Length Promoter (1981)   ATCAACCAATCCATAACTCGAAACCTTTTC
                                          2011                           2040
SEQ ID NO:2 Truncated Promoter   (1448)   TTGTGCTCTGTTCTGTCTGTGTGTTTCCAA
SEQ ID NO:1 Full Length Promoter (2011)   TTGTGCTCTGTTCTGTCTGTGTGTTTCCAA
                                          2041            2061
SEQ ID NO:2 Truncated Promoter   (1478)   AGCAAACGAAAGAGGTCGAGG
SEQ ID NO:1 Full Length Promoter (2041)   AGCAAACGAAAGAGGTCGAGG
```

Fig. 8A

|  |  | 1 | 30 |
|---|---|---|---|
| SEQ ID NO:3 Full Length 3'-UTR | (1) | TCCTGCTGCGTTGTTTCGTTTGCGGCATGC | |
| SEQ ID NO:4 Truncated 3'-UTR | (1) | TCCTGCTGCGTTGTTTCGTTTGCGGCATGC | |
|  |  | 31 | 60 |
| SEQ ID NO:3 Full Length 3'-UTR | (31) | ATGGATGTCACCTTTTTTTACTGTCTGCT | |
| SEQ ID NO:4 Truncated 3'-UTR | (31) | ATGGATGTCACCTTTTTTTACTGTCTGCT | |
|  |  | 61 | 90 |
| SEQ ID NO:3 Full Length 3'-UTR | (61) | TTGTGCTTGTGGCGTGTCAAGAATAAAGGA | |
| SEQ ID NO:4 Truncated 3'-UTR | (61) | TTGTGCTTGTGGCGTGTCAAGAATAAAGGA | |
|  |  | 91 | 120 |
| SEQ ID NO:3 Full Length 3'-UTR | (91) | TGGAGCCATCGTCTGGTCTGACTCTGGCTC | |
| SEQ ID NO:4 Truncated 3'-UTR | (91) | TGGAGCCATCGTCTGGTCTGACTCTGGCTC | |
|  |  | 121 | 150 |
| SEQ ID NO:3 Full Length 3'-UTR | (121) | CCGCCATGCATGCTGGTGTCGGTTCTGT | |
| SEQ ID NO:4 Truncated 3'-UTR | (121) | CCGCCATGCATGCTGGTGTCGGTTCTGT | |
|  |  | 151 | 180 |
| SEQ ID NO:3 Full Length 3'-UTR | (151) | GGTGCTTGTCTTGGTCCATGTAATCTATG | |
| SEQ ID NO:4 Truncated 3'-UTR | (151) | GGTGCTTGTCTTGGTCCATGTAATCTATG | |
|  |  | 181 | 210 |
| SEQ ID NO:3 Full Length 3'-UTR | (181) | GCATCGTTACACACCATGCATCTCTGATCT | |
| SEQ ID NO:4 Truncated 3'-UTR | (181) | GCATCGTTACACACCATGCATCTCTGATCT | |
|  |  | 211 | 240 |
| SEQ ID NO:3 Full Length 3'-UTR | (211) | CTTTGCGCCAGTGTGTGTGACTATGTCCGT | |
| SEQ ID NO:4 Truncated 3'-UTR | (211) | CTTTGCGCCAGTGTGTGTGACTATGTCCGT | |
|  |  | 241 | 270 |
| SEQ ID NO:3 Full Length 3'-UTR | (241) | GTAACGATTGGCTCAGTGATTGAATATATA | |
| SEQ ID NO:4 Truncated 3'-UTR | (241) | GTAACGATTGGCTCAGTGATTGAATATATA | |
|  |  | 271 | 300 |
| SEQ ID NO:3 Full Length 3'-UTR | (271) | TACAATACTGTTTTACTAAGTAAGTATGAT | |
| SEQ ID NO:4 Truncated 3'-UTR | (271) | TACAATACTGTTTTACTAAGTAAGTATGAT | |
|  |  | 301 | 330 |
| SEQ ID NO:3 Full Length 3'-UTR | (301) | TACCTCTTATTTAAATTTCTCTATGTAAA | |
| SEQ ID NO:4 Truncated 3'-UTR | (301) | TACCTCTTATTTAAATTTCTCTATGTAAA | |
|  |  | 331 | 360 |
| SEQ ID NO:3 Full Length 3'-UTR | (331) | TCATGTCTTCTACACAGTATGTTGTACGAC | |
| SEQ ID NO:4 Truncated 3'-UTR | (331) | TCATGTCTTCTACACAGTATGTTGTACGAC | |
|  |  | 361 | 390 |
| SEQ ID NO:3 Full Length 3'-UTR | (361) | CACTATCTGCTGAATGTATAGATGTCTAGA | |
| SEQ ID NO:4 Truncated 3'-UTR | (361) | CACTATCTGCTGAATG-------------- | |
|  |  | 391 | 420 |
| SEQ ID NO:3 Full Length 3'-UTR | (391) | AAGCACGTGGCCCGTTAGCATGACACGAAG | |
| SEQ ID NO:4 Truncated 3'-UTR | (377) | ------------------------------ | |
|  |  | 421 | 450 |
| SEQ ID NO:3 Full Length 3'-UTR | (421) | CACGGTTTTTTAGCACGACACAAATTAACA | |
| SEQ ID NO:4 Truncated 3'-UTR | (377) | ------------------------------ | |
|  |  | 451 | 480 |
| SEQ ID NO:3 Full Length 3'-UTR | (451) | TGGGCCCAGGCTCAGCCCGGCCCAGCGAGC | |
| SEQ ID NO:4 Truncated 3'-UTR | (377) | ------------------------------ | |
|  |  | 481 | 510 |
| SEQ ID NO:3 Full Length 3'-UTR | (481) | GTGTCGGGCTCGACAGCCATCCCGACGCGT | |
| SEQ ID NO:4 Truncated 3'-UTR | (377) | ------------------------------ | |
|  |  | 511 | 540 |
| SEQ ID NO:3 Full Length 3'-UTR | (511) | TGGGCTGGCCCGAGCACGGCCCGGTGGATG | |
| SEQ ID NO:4 Truncated 3'-UTR | (377) | ------------------------------ | |
|  |  | 541 | 570 |
| SEQ ID NO:3 Full Length 3'-UTR | (541) | TTGGGCTTAGAAACCGGCCCGCTACATTTT | |

Fig. 8B

```
SEQ ID NO:4 Truncated 3'-UTR    (377) ------------------------------
                                       571                        600
SEQ ID NO:3 Full Length 3'-UTR  (571) AGCGCAGCCTAACCCACTGCCCACCAATAC
SEQ ID NO:4 Truncated 3'-UTR    (377) ------------------------------
                                       601                        630
SEQ ID NO:3 Full Length 3'-UTR  (601) TCCGCAATTCCGCATAAATCCCCCAGTGCC
SEQ ID NO:4 Truncated 3'-UTR    (377) ------------------------------
                                       631                        660
SEQ ID NO:3 Full Length 3'-UTR  (631) CCATCCCCAGCCCATTGACCAGCGCGACAG
SEQ ID NO:4 Truncated 3'-UTR    (377) ------------------------------
                                       661                        690
SEQ ID NO:3 Full Length 3'-UTR  (661) CTAGGGCTGGAAAAAAAGCTCGAGGCTCGC
SEQ ID NO:4 Truncated 3'-UTR    (377) ------------------------------
                                       691                        720
SEQ ID NO:3 Full Length 3'-UTR  (691) GAGCCAGCTCGGGCTCGATCAGGCTCGGCT
SEQ ID NO:4 Truncated 3'-UTR    (377) ------------------------------
                                       721                        750
SEQ ID NO:3 Full Length 3'-UTR  (721) CGGCTCGGTGAGGCTCGCGAGCCTAAACGA
SEQ ID NO:4 Truncated 3'-UTR    (377) ------------------------------
                                       751                        780
SEQ ID NO:3 Full Length 3'-UTR  (751) GCCCGAGCCGAGCCTAATTCCGCAGCTCGC
SEQ ID NO:4 Truncated 3'-UTR    (377) ------------------------------
                                       781                        810
SEQ ID NO:3 Full Length 3'-UTR  (781) TACACTAACGAGCCGAGCCGGCTTGGTGAG
SEQ ID NO:4 Truncated 3'-UTR    (377) ------------------------------
                                       811                        840
SEQ ID NO:3 Full Length 3'-UTR  (811) GCTCGCGAGCGGGCTCAAGGCTTGGTCCAA
SEQ ID NO:4 Truncated 3'-UTR    (377) ------------------------------
                                       841                        870
SEQ ID NO:3 Full Length 3'-UTR  (841) ACTACTACTTACTCGTATCTCCGTTCACCA
SEQ ID NO:4 Truncated 3'-UTR    (377) ------------------------------
                                       871                        900
SEQ ID NO:3 Full Length 3'-UTR  (871) GTGTGTAAGTGTGCTGTTTTGGTCACAACT
SEQ ID NO:4 Truncated 3'-UTR    (377) ------------------------------
                                       901                        930
SEQ ID NO:3 Full Length 3'-UTR  (901) CACAAGGAACTAGAGTGCAGGGACATAATT
SEQ ID NO:4 Truncated 3'-UTR    (377) ------------------------------
                                       931                        960
SEQ ID NO:3 Full Length 3'-UTR  (931) TTTTATTATATGGAACATATTGTGCTTCAA
SEQ ID NO:4 Truncated 3'-UTR    (377) ------------------------------
                                       961                        990
SEQ ID NO:3 Full Length 3'-UTR  (961) ATTTGAGCTAATGACTATAATTATTGTTGT
SEQ ID NO:4 Truncated 3'-UTR    (377) ------------------------------
                                       991                       1020
SEQ ID NO:3 Full Length 3'-UTR  (991) TGAGTACTTGAGTGTACAGGCTCGCGAGCC
SEQ ID NO:4 Truncated 3'-UTR    (377) ------------------------------
                                      1021                       1050
SEQ ID NO:3 Full Length 3'-UTR (1021) TATATCGAGCCGAGCCTCATTACCGAGCTC
SEQ ID NO:4 Truncated 3'-UTR    (377) ------------------------------
                                      1051                       1080
SEQ ID NO:3 Full Length 3'-UTR (1051) GCTAAGTGACCGAGCCGAGCCTGGCTCGGC
SEQ ID NO:4 Truncated 3'-UTR    (377) ------------------------------
```

ZEA MAYS METALLOTHIONEIN-LIKE REGULATORY ELEMENTS AND USES THEREOF

CROSS REFERENCE TO RELATED APPLICATIONS

This application claims priority under 35 U.S.C. §119(e) of U.S. Provisional Application No. 61/886,943, filed Oct. 4, 2013, which is hereby incorporated by reference in its entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: One 16 KB ACII (Text) file named "224883_ST25" created on Sep. 29, 2014.

BACKGROUND

Plant transformation is an attractive technology for use in introducing agronomically desirable traits or characteristics into different crop plant species. Plant species are developed and/or modified to have particular desirable traits. Generally, desirable traits include, for example, improving nutritional value quality, increasing yield, conferring pest or disease resistance, increasing drought and stress tolerance, improving horticultural qualities (e.g., pigmentation and growth), imparting herbicide resistance, enabling the production of industrially useful compounds and/or materials from the plant, and/or enabling the production of pharmaceuticals.

Transgenic plans comprising multiple transgenes stacked at a single genomic locus are produced via plant transformation technologies. Plant transformation technologies result in the introduction of a transgenes into a plant cell, recovery of a fertile transgenic plant that contains the stably integrated copy of the transgene in the plant genome, and subsequent transgene expression via transcription and translation of the transgene(s) results in transgenic plants that possess desirable traits and phenotypes. Each transgene in a stack typically requires an independent promoter for gene expression, and thus multiple promoters are used in a transgene stack.

The need for co-expression of multiple transgenes for regulating the same trait frequently results in the repeated use of the same promoter to drive expression of the multiple transgenes. However, the repeated use of promoters comprising sequences that share a high level of sequence identity may lead to homology-based gene silencing (HBGS). HBGS has been observed to occur frequently in transgenic plants (Peremarti et al., 2010) when repetitive DNA sequences are used within a transgene. In addition, repeated use of similar DNA sequences in transgene constructs has proven to be challenging in *Agrobacterium* due to recombination and instability of the plasmid.

Described herein are *Zea mays* metallothionein-like gene regulatory elements (e.g., promoters, 5'-UTR, and 3'-UTR). Further described are constructs and methods utilizing *Zea mays* metallothionein-like gene regulatory elements.

SUMMARY

Disclosed herein are constructs and methods for expressing a transgene in plant cells and/or plant tissues. In one embodiment, regulatory elements of a *Zea mays* metallothionein-like gene are purified from a maize genome and recombined with sequences not natively linked to said regulatory elements to create an expression vector for expressing transgenes in plant cells not native to the *Zea mays* metallothionein-like regulatory sequences. In one embodiment an expression vector is provided wherein the regulatory elements of a *Zea mays* metallothionein-like gene are operably linked to a polylinker sequence. Such an expression vector eases the insertion of a gene or gene cassette into the vector in an operably linked state with the *Zea mays* metallothionein-like gene regulatory sequences.

In an embodiment, a construct is provided comprising a *Zea mays* metallothionein-like promoter. In an embodiment, a gene expression cassette is provided comprising a *Zea mays* metallothionein-like promoter operably linked to a transgene. In an embodiment, a gene expression cassette includes a *Zea mays* metallothionein-like 3'-UTR operably linked to a transgene. In an embodiment, a gene expression cassette includes a *Zea mays* metallothionein-like 3'-UTR operably linked to a promoter. In an embodiment, a gene expression cassette includes a *Zea mays* metallothionein-like 5'-UTR operably linked to a transgene. In an embodiment, a gene expression cassette includes a *Zea mays* metallothionein-like 5'-UTR operably linked to a promoter. In an embodiment, a gene expression cassette includes at least one, two, three, five, six, seven, eight, nine, ten, or more transgenes.

In an embodiment, a gene expression cassette includes independently a) a *Zea mays* metallothionein-like promoter, b) a *Zea mays* metallothionein-like 5'-UTR, and c) a *Zea mays* metallothionein-like 3'-UTR.

In accordance with one embodiment a nucleic acid vector is provided comprising a promoter operably linked to a transgene, wherein the promoter consists of SEQ ID NO: 1 or a sequence having 90% sequence identity with SEQ ID NO: 1. In a further embodiment the nucleic acid vector comprises a gene cassette, wherein the gene cassette comprises a promoter, a transgene and a 3' untranslated region, wherein the promoter consists of SEQ ID NO: 1 operably linked to a first end of a transgene, wherein the second end of the transgene is operably linked to a 3' untranslated sequence consisting of SEQ ID NO: 3. In a further embodiment the nucleic acid vector comprises a gene cassette, wherein the gene cassette comprises a promoter, a transgene and a 3' untranslated region, wherein the promoter consists of SEQ ID NO: 1 operably linked to a first end of a transgene, wherein the second end of the transgene is operably linked to a 3' untranslated sequence consisting of SEQ ID NO: 4.

In accordance with one embodiment a nucleic acid vector is provided comprising a promoter operably linked to a transgene, wherein the promoter consists of SEQ ID NO: 2 or a sequence having 90% sequence identity with SEQ ID NO: 2. In a further embodiment the nucleic acid vector comprises a gene cassette, wherein the gene cassette comprises a promoter, a transgene and a 3' untranslated region, wherein the promoter consists of SEQ ID NO: 2 operably linked to a first end of a transgene, wherein the second end of the transgene is operably linked to a 3' untranslated sequence consisting of SEQ ID NO: 3. In a further embodiment the nucleic acid vector comprises a gene cassette, wherein the gene cassette comprises a promoter, a transgene and a 3' untranslated region, wherein the promoter consists of SEQ ID NO: 2 operably linked to a first end of a transgene, wherein the second end of the transgene is operably linked to a 3' untranslated sequence consisting of SEQ ID NO: 4.

Methods of growing plants expressing a transgene using *Zea mays* metallothionein-like promoters, 5'-UTRs, and 3'-UTRs are disclosed herein. Methods of culturing plant tissues and cells expressing a transgene using the *Zea mays* metallothionein-like promoters, 5'-UTRs, and 3'-UTRs are also disclosed herein. In an embodiment, methods as disclosed herein include tissue-specific gene expression in plant roots.

In accordance with one embodiment a plant, plant tissue, or plant cell is provided comprising a promoter operably linked to a transgene, wherein the promoter comprises SEQ ID NO: 1. In accordance with one embodiment a non-*Zea mays* plant or plant cell is provided comprising SEQ ID NO: 1, or a sequence that has 90% sequence identity with SEQ ID NO: 1 operably linked to a transgene. In accordance with another embodiment a plant, plant tissue, or plant cell is provided comprising a promoter operably linked to a transgene, wherein the promoter comprises SEQ ID NO: 2. In accordance with one embodiment a non-*Zea mays* plant or plant cell is provided comprising SEQ ID NO: 2, or a sequence that has 90% sequence identity with SEQ ID NO: 2 operably linked to a transgene.

In one embodiment the plant is a corn variety. In one embodiment a plant, plant tissue, or plant cell is provided comprising a promoter operably linked to a transgene, wherein the promoter consists of SEQ ID NO: 1 or 2. In one embodiment a non-*Zea mays* plant or plant cell is provided comprising a gene cassette, wherein the gene cassette comprises a promoter operably linked to a transgene, further wherein the promoter consists SEQ ID NO: 1. In another embodiment a non-*Zea mays* plant or plant cell is provided comprising a gene cassette, wherein the gene cassette comprises a promoter operably linked to a transgene, further wherein the promoter consists SEQ ID NO: 2. In a further embodiment the promoter is operably linked to a first end of a transgene, wherein the second end of the transgene is operably linked to a 3' untranslated sequence consisting of SEQ ID NO: 3. In yet a further embodiment the promoter is operably linked to a first end of a transgene, wherein the second end of the transgene is operably linked to a 3' untranslated sequence consisting of SEQ ID NO: 4.

BRIEF DESCRIPTION OF THE DRAWINGS

FIGS. 6A-6D show an alignment of the truncated *Zea mays* metallothionein-like promoter and the full length *Zea mays* metallothionein-like promoter.

FIGS. 8A-8B show an alignment of the truncated *Zea mays* metallothionein-like 3'-UTR and the full length *Zea mays* metallothionein-like 3'-UTR.

DETAILED DESCRIPTION

Definitions

Figure 1:
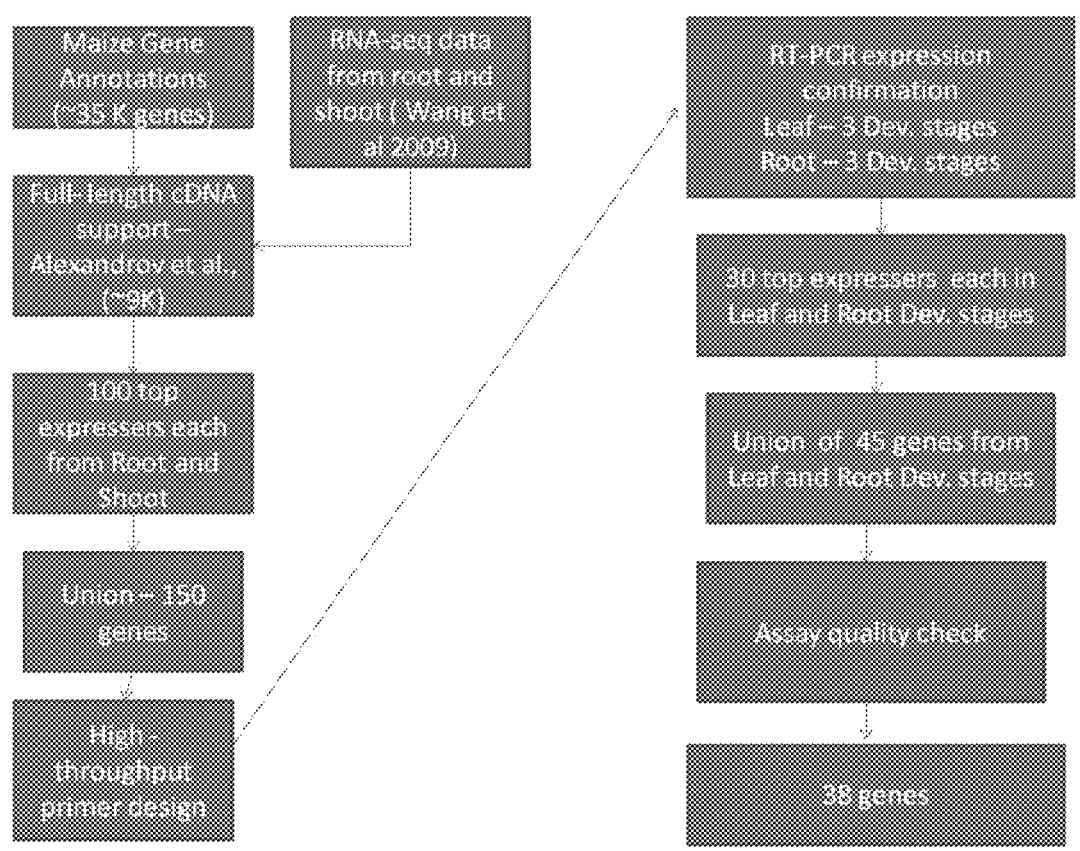
FIG. 1 is a schematic flow chart displaying the process of identifying high expressing genes in maize using a bioinformatics approach to analyze genomic sequence data obtained from a database.

In describing and claiming the invention, the following terminology will be used in accordance with the definitions set forth below.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein, the term "backcrossing" refers to a process in which a breeder crosses hybrid progeny back to one of the parents, for example, a first generation hybrid F1 with one of the parental genotypes of the F1 hybrid.

A "promoter" is a DNA regulatory region capable of binding RNA polymerase in a cell and initiating transcription of a downstream (3' direction) coding sequence. A promoter may contain specific sequences that are recognized by transcription factors. These factors may bind to a promoter DNA sequence, which results in the recruitment of RNA polymerase. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. The promoter may be operatively associated with other expression control sequences, including enhancer and repressor sequences.

For the purposes of the present disclosure, a "gene," includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

As used herein a "transgene" is defined to be a nucleic acid sequence that encodes a gene product, including for example, but not limited to, an mRNA. In one embodiment the transgene is an exogenous nucleic acid, where the transgene sequence has been introduced into a host cell by genetic engineering (or the progeny thereof) where the transgene is not normally found. In one example, a transgene encodes an industrially or pharmaceutically useful compound, or a gene encoding a desirable agricultural trait (e.g., an herbicide-resistance gene). In yet another example, a transgene is an antisense nucleic acid sequence, wherein expression of the antisense nucleic acid sequence inhibits expression of a target nucleic acid sequence. In one embodiment the transgene is an endogenous nucleic acid, wherein additional genomic copies of the endogenous nucleic acid are desired, or a nucleic acid that is in the antisense orientation with respect to the sequence of a target nucleic acid in a host organism.

"Gene expression" as defined herein is the conversion of the information, contained in a gene, into a gene product.

A "gene product" as defined herein is any product produced by the gene. For example the gene product can be the direct transcriptional product of a gene (e.g., mRNA, tRNA, rRNA, antisense RNA, interfering RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation. Gene expression can be influenced by external signals, for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein, the term "intron" is defined as any nucleic acid sequence comprised in a gene (or expressed nucleotide sequence of interest) that is transcribed but not translated. Introns include untranslated nucleic acid sequence within an expressed sequence of DNA, as well as corresponding sequence in RNA molecules transcribed therefrom.

A construct described herein can also contain sequences that enhance translation and/or mRNA stability such as introns. An example of one such intron is the first intron of gene II of the histone H3 variant of Arabidopsis thaliana or any other commonly known intron sequence. Introns can be used in combination with a promoter sequence to enhance translation and/or mRNA stability.

As used herein, the terms "5' untranslated region" or "5'-UTR" is defined as the untranslated segment in the 5' terminus of pre-mRNAs or mature mRNAs. For example, on mature mRNAs, a 5'-UTR typically harbors on its 5' end a 7-methylguanosine cap and is involved in many processes such as splicing, polyadenylation, mRNA export towards the cytoplasm, identification of the 5' end of the mRNA by the translational machinery, and protection of the mRNAs against degradation.

As used herein, the terms "transcription terminator" is defined as the transcribed segment in the 3' terminus of pre-mRNAs or mature mRNAs. For example, longer stretches of DNA beyond "polyadenylation signal" site is transcribed as a pre-mRNA. This DNA sequence usually contains one or more transcription termination signals for the proper processing of the pre-mRNA into mature mRNA.

As used herein, the term "3' untranslated region" or "3'-UTR" is defined as the untranslated segment in a 3' terminus of the pre-mRNAs or mature mRNAs. For example, on mature mRNAs this region harbors the poly-(A) tail and is known to have many roles in mRNA stability, translation initiation, and mRNA export.

As used herein, the term "polyadenylation signal" designates a nucleic acid sequence present in mRNA transcripts that allows for transcripts, when in the presence of a poly-(A) polymerase, to be polyadenylated on the polyadenylation site, for example, located 10 to 30 bases downstream of the poly-(A) signal. Many polyadenylation signals are known in the art and are useful for the present invention. An exemplary sequence includes AAUAAA and variants thereof, as described in Loke J., et al., (2005) *Plant Physiology* 138(3); 1457-1468.

The term "isolated" as used herein means having been removed from its natural environment, or removed from other compounds present when the compound is first formed. The term "isolated" embraces materials isolated from natural sources as well as materials (e.g., nucleic acids and proteins) recovered after preparation by recombinant expression in a host cell, or chemically-synthesized compounds such as nucleic acid molecules, proteins, and peptides.

The term "purified," as used herein relates to the isolation of a molecule or compound in a form that is substantially free of contaminants normally associated with the molecule or compound in a native or natural environment, or substantially enriched in concentration relative to other compounds present when the compound is first formed, and means having been increased in purity as a result of being separated from other components of the original composition. The term "purified nucleic acid" is used herein to describe a nucleic acid sequence which has been separated, produced apart from other biological compounds including, but not limited to polypeptides, lipids and carbohydrates, while effecting a chemical or functional change in the component (e.g., a nucleic acid may be purified from a chromosome by removing protein contaminants and breaking chemical bonds connecting the nucleic acid to the remaining DNA in the chromosome).

The term "recombinant" means a cell or organism in which genetic recombination has occurred. It also includes a molecule (e.g., a vector, plasmid, nucleic acid or a polypeptide) that has been artificially or synthetically (i.e., non-naturally) altered by human intervention. The alteration can be performed on the molecule within, or removed from, its natural environment or state.

As used herein, the terms "homology-based gene silencing" or "HBGS" are generic terms that include both transcriptional gene silencing and post-transcriptional gene silencing. Silencing of a target locus by an unlinked silencing locus can result from transcription inhibition (transcriptional gene silencing; TGS) or mRNA degradation (post-transcriptional gene silencing; PTGS), owing to the production of double-stranded RNA (dsRNA) corresponding to promoter or transcribed sequences, respectively. Involvement of distinct cellular components in each process suggests that dsRNA-induced TGS and PTGS likely result from the diversification of an ancient common mechanism. However, a strict comparison of TGS and PTGS has been difficult to achieve because it generally relies on the analysis of distinct silencing loci. A single transgene locus can be described to trigger both TGS and PTGS, owing to the production of dsRNA corresponding to promoter and transcribed sequences of different target genes.

As used herein, the terms "nucleic acid molecule", "nucleic acid", or "polynucleotide" (all three terms are synonymous with one another) refer to a polymeric form of nucleotides, which may include both sense and anti-sense strands of RNA, cDNA, genomic DNA, and synthetic forms, and mixed polymers thereof. "A nucleotide" may refer to a ribonucleotide, deoxyribonucleotide, or a modified form of either type of nucleotide. A nucleic acid molecule is usually at least 10 bases in length, unless otherwise specified. The terms may refer to a molecule of RNA or DNA of indeterminate length. The terms include single- and double-stranded forms of DNA. A nucleic acid molecule may include either or both naturally-occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Transcription proceeds in a 5' to 3' manner along a DNA strand. This means that RNA is made by sequential addition of ribonucleotide-5'-triphosphates to the 3' terminus of the growing chain (with a requisite elimination of the pyrophosphate). In either a linear or circular nucleic acid molecule, discrete elements (e.g., particular nucleotide sequences) may be referred to as being "upstream" relative to a further element if they are bonded or would be bonded to the same nucleic acid in the 5' direction from that element. Similarly, discrete elements may be "downstream" relative to a further element if they are or would be bonded to the same nucleic acid in the 3' direction from that element.

As used herein, the term "base position" refers to the location of a given base or nucleotide residue within a designated nucleic acid. A designated nucleic acid may be defined by alignment with a reference nucleic acid.

As used herein, the term "hybridization" refers to a process where oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and bonding of a pyrimidine to a purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

As used herein, the terms "specifically hybridizable" and "specifically complementary" refers to a sufficient degree of complementarity such that stable and specific binding occurs between an oligonucleotide and the DNA or RNA target. Oligonucleotides need not be 100% complementary to the target sequence to specifically hybridize. An oligonucleotide is specifically hybridizable when binding of the oligonucleotide to the target DNA or RNA molecule interferes with the normal function of the target DNA or RNA, and there is sufficient degree of complementarity to avoid non-specific binding of an oligonucleotide to non-target sequences under conditions where specific binding is desired, for example under physiological conditions in the case of in vivo assays or systems. Such binding is referred to as specific hybridization. Hybridization conditions resulting in particular degrees of stringency will vary depending upon the nature of the chosen hybridization method and the composition and length of the hybridizing nucleic acid sequences. Generally, the temperature of hybridization and the ionic strength (especially $Na^+$ and/or $Mg^{2+}$ concentration) of a hybridization buffer will contribute to the stringency of hybridization, though wash times also influence stringency. Calculations regarding hybridization conditions required for attaining particular degrees of stringency are discussed in Sambrook et al. (ed.), Molecular Cloning: A Laboratory Manual, 2nd ed., vol. 1-3, Cold Spring Harbor Laboratory Press, Cold Spring Harbor, N.Y., 1989.

As used herein, the term "stringent conditions" encompasses conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize.

In particular embodiments, stringent conditions can include hybridization at 65° C., followed by washes at 65° C. with 0.1×SSC/0.1% SDS for 40 minutes. The following are representative, non-limiting hybridization conditions:

Very High Stringency: hybridization in 5×SSC buffer at 65° C. for 16 hours; wash twice in 2×SSC buffer at room temperature for 15 minutes each; and wash twice in 0.5× SSC buffer at 65° C. for 20 minutes each.

High Stringency: Hybridization in 5-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Moderate Stringency: Hybridization in 6×SSC buffer at room temperature to 55° C. for 16-20 hours; wash at least twice in 2-3×SSC buffer at room temperature to 55° C. for 20-30 minutes each.

In an embodiment, specifically hybridizable nucleic acid molecules can remain bound under very high stringency hybridization conditions. In an embodiment, specifically hybridizable nucleic acid molecules can remain bound under high stringency hybridization conditions. In an embodiment, specifically hybridizable nucleic acid molecules can remain bound under moderate stringency hybridization conditions.

As used herein, the term "oligonucleotide" refers to a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in polymerase chain reaction, a technique for the amplification of small DNA sequences. In polymerase chain reaction, an oligonucleotide is typically referred to as a "primer" which allows a DNA polymerase to extend the oligonucleotide and replicate the complementary strand.

As used herein, the terms "Polymerase Chain Reaction" or "PCR" define a procedure or technique in which minute amounts of nucleic acid, RNA and/or DNA, are amplified as described in U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51:263 (1987); Erlich, ed., PCR Technology, (Stockton Press, NY, 1989).

As used herein, the term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, that may include constituents which are co-factors or which affect conditions such as pH and the like at various suitable temperatures. A primer is preferably a single strand sequence, such that amplification efficiency is optimized, but double stranded sequences can be utilized.

As used herein, the term "probe" refers to an oligonucleotide or polynucleotide sequence that hybridizes to a target sequence. In the TaqMan® or TaqMan®-style assay procedure, the probe hybridizes to a portion of the target situated between the annealing site of the two primers. A probe includes about eight nucleotides, about ten nucleotides, about fifteen nucleotides, about twenty nucleotides, about thirty nucleotides, about forty nucleotides, or about fifty nucleotides. In some embodiments, a probe includes from about eight nucleotides to about fifteen nucleotides.

In the Southern blot assay procedure, the probe hybridizes to a DNA fragment that is attached to a membrane. A probe includes about ten nucleotides, about 100 nucleotides, about 250 nucleotides, about 500 nucleotides, about 1,000 nucleotides, about 2,500 nucleotides, or about 5,000 nucleotides. In some embodiments, a probe includes from about 500 nucleotides to about 2,500 nucleotides.

A probe can further include a detectable label, e.g., a radioactive label, a biotinylated label, a fluorophore (Texas-Red®, Fluorescein isothiocyanate, etc.,). The detectable label can be covalently attached directly to the probe oligonucleotide, e.g., located at the probe's 5' end or at the probe's 3' end. A probe including a fluorophore may also further include a quencher, e.g., Black Hole Quencher™, Iowa Black™, etc.

As used herein, the terms "sequence identity" or "identity" can be used interchangeably and refer to nucleic acid residues in two sequences that are the same when aligned for maximum correspondence over a specified comparison window.

As used herein, the term "percentage of sequence identity" refers to a value determined by comparing two optimally aligned sequences (e.g., nucleic acid sequences or amino acid sequences) over a comparison window, wherein the portion of a sequence in the comparison window may comprise additions or deletions (i.e., gaps) as compared to a reference sequence (that does not comprise additions or deletions) for optimal alignment of the two sequences. A percentage is calculated by determining the number of positions at which an identical nucleic acid or amino acid residue occurs in both sequences to yield the number of matched positions, dividing the number of matched positions by the total number of positions in the comparison window, and multiplying the result by 100 to yield the percentage of sequence identity. Methods for aligning sequences for comparison are well known. Various programs and alignment algorithms are described in, for example: Smith and Waterman (1981) *Adv. Appl. Math.* 2:482; Needleman and Wunsch (1970) *J. Mol. Biol.* 48:443; Pearson and Lipman (1988) *Proc. Natl. Acad. Sci. U.S.A.* 85:2444; Higgins and Sharp (1988) *Gene* 73:237-44; Higgins and Sharp (1989) *CABIOS* 5:151-3; Corpet et al. (1988) *Nucleic Acids Res.* 16:10881-90; Huang et al. (1992) *Comp. Appl. Biosci.* 8:155-65; Pearson et al. (1994) *Methods Mol. Biol.* 24:307-31; Tatiana et al. (1999) *FEMS Microbiol. Lett.* 174:247-50.

The National Center for Biotechnology Information (NCBI) Basic Local Alignment Search Tool (BLAST™; Altschul et al. (1990) *J. Mol. Biol.* 215:403-10) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method.

As used herein, the term "operably linked" refers to two components that have been placed into a functional relationship with one another. The term, "operably linked," when used in reference to a regulatory sequence and a coding sequence, means that the regulatory sequence affects the expression of the linked coding sequence. "Regulatory sequences," "regulatory elements", or "control elements," refer to nucleic acid sequences that influence the timing and level/amount of transcription, RNA processing or stability, or translation of the associated coding sequence. Regulatory sequences may include promoters; translation leader sequences; 5' and 3' untranslated regions, introns; enhancers; stem-loop structures; repressor binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule. Linking can be accomplished by ligation at convenient restriction sites. If such sites do not exist, synthetic oligonucleotide adaptors or linkers are ligated or annealed to the nucleic acid and used to link the contiguous polynucleotide fragment. However, elements need not be contiguous to be operably linked.

As used herein, the term "transformation" encompasses all techniques that a nucleic acid molecule can be introduced into such a cell. Examples include, but are not limited to: transfection with viral vectors; transformation with plasmid vectors; electroporation; lipofection; microinjection (Mueller et al. (1978) Cell 15:579-85); Agrobacterium-mediated transfer; direct DNA uptake; WHISKERS™-mediated transformation; and microprojectile bombardment. These techniques may be used for both stable transformation and transient transformation of a plant cell. "Stable transformation" refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms. "Transient transformation" refers to the introduction of a nucleic acid fragment into the nucleus, or DNA-containing organelle, of a host organism resulting in gene expression without genetically stable inheritance.

As used herein, the term "transduce" refers to a process where a virus transfers nucleic acid into a cell.

The terms "polylinker" or "multiple cloning site" as used herein defines a cluster of three or more Type-2 restriction enzyme sites located within 10 nucleotides of one another on a nucleic acid sequence. Constructs comprising a polylinker are utilized for the insertion and/or excision of nucleic acid sequences such as the coding region of a gene.

As used herein, the terms "restriction endonucleases" and "restriction enzymes" refer to bacterial enzymes, each of which cut double-stranded DNA at or near a specific nucleotide sequence. Type-2 restriction enzymes recognize and cleave DNA at the same site, and include but are not limited to XbaI, BamHI, HindIII, EcoRI, XhoI, SalI, KpnI, AvaI, PstI and SmaI.

The term "vector" is used interchangeably with the terms "construct", "cloning vector" and "expression vector" and means the vehicle by which a DNA or RNA sequence (e.g. a foreign gene) can be introduced into a host cell, so as to transform the host and promote expression (e.g. transcription and translation) of the introduced sequence. A "non-viral vector" is intended to mean any vector that does not comprise a virus or retrovirus. In some embodiments a "vector" is a sequence of DNA comprising at least one origin of DNA replication and at least one selectable marker gene. Examples include, but are not limited to, a plasmid, cosmid, bacteriophage, bacterial artificial chromosome (BAC), or virus that carries exogenous DNA into a cell. A vector can also include one or more genes, antisense molecules, and/or selectable marker genes and other genetic elements known in the art. A vector may transduce, transform, or infect a cell, thereby causing the cell to express the nucleic acid molecules and/or proteins encoded by the vector. The term "plasmid" defines a circular strand of nucleic acid capable of autosomal replication in either a prokaryotic or a eukaryotic host cell. The term includes nucleic acid which may be either DNA or RNA and may be single- or double-stranded. The plasmid of the definition may also include the sequences which correspond to a bacterial origin of replication.

The term "selectable marker gene" as used herein defines a gene or other expression cassette which encodes a protein which facilitates identification of cells into which the selectable marker gene is inserted. For example a "selectable marker gene" encompasses reporter genes as well as genes used in plant transformation to, for example, protect plant cells from a selective agent or provide resistance/tolerance to a selective agent. In one embodiment only those cells or plants that receive a functional selectable marker are capable of dividing or growing under conditions having a selective agent. Examples of selective agents can include, for example, antibiotics, including spectinomycin, neomycin, kanamycin, paromomycin, gentamicin, and hygromycin. These selectable markers include neomycin phosphotransferase (npt II), which expresses an enzyme conferring resistance to the antibiotic kanamycin, and genes for the related antibiotics neomycin, paromomycin, gentamicin, and G418, or the gene for hygromycin phosphotransferase (hpt), which expresses an enzyme conferring resistance to hygromycin. Other selectable marker genes can include genes encoding herbicide resistance including bar or pat (resistance against glufosinate ammonium or phosphinothricin), acetolactate synthase (ALS, resistance against inhibitors such as sulfonylureas (SUs), imidazolinones (IMIs), triazolopyrimidines (TPs), pyrimidinyl oxybenzoates (POBs), and sulfonylamino carbonyl triazolinones that prevent the first step in the synthesis of the branched-chain amino acids), glyphosate, 2,4-D, and metal resistance or sensitivity. Examples of "reporter genes" that can be used as a selectable marker gene include the visual observation of expressed reporter gene proteins such as proteins encoding β-glucuronidase (GUS), luciferase, green fluorescent protein (GFP), yellow fluorescent protein (YFP), DsRed, β-galactosidase, chloramphenicol acetyltransferase (CAT), alkaline phosphatase, and the like. The phrase "marker-positive" refers to plants that have been transformed to include a selectable marker gene.

As used herein, the term "detectable marker" refers to a label capable of detection, such as, for example, a radioisotope, fluorescent compound, bioluminescent compound, a chemiluminescent compound, metal chelator, or enzyme. Examples of detectable markers include, but are not limited to, the following: fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In an embodiment, a detectable marker can be attached by spacer arms of various lengths to reduce potential steric hindrance.

As used herein, the term "detecting" is used in the broadest sense to include both qualitative and quantitative measurements of a specific molecule, for example, measurements of a specific polypeptide.

As used herein, the terms "cassette", "expression cassette" and "gene expression cassette" refer to a segment of DNA that can be inserted into a nucleic acid or polynucleotide at specific restriction sites or by homologous recombination. As used herein the segment of DNA comprises a polynucleotide containing a gene of interest that encodes a polypeptide of interest, and the cassette and restriction sites are designed to ensure insertion of the cassette in the proper reading frame for transcription and translation. In an embodiment, an expression cassette can include a polynucleotide that encodes a polypeptide of interest and having elements in addition to the polynucleotide that facilitate transformation of a particular host cell. In an embodiment, a gene expression cassette may also include elements that allow for enhanced expression of a polynucleotide encoding a polypeptide of interest in a host cell. These elements may include, but are not limited to: a promoter, a minimal promoter, an enhancer, a response element, an intron, a 5' untranslated region sequence, a 3' untranslated region sequence, a terminator sequence, a polyadenylation sequence, and the like.

As used herein a "linker" or "spacer" is a bond, molecule or group of molecules that binds two separate entities to one another. Linkers and spacers may provide for optimal spacing of the two entities or may further supply a labile linkage that allows the two entities to be separated from each other. Labile linkages include photocleavable groups, acid-labile moieties, base-labile moieties and enzyme-cleavable groups.

As used herein, the term "heterologous coding sequence" is used to indicate any polynucleotide that codes for, or ultimately codes for, a peptide or protein or its equivalent amino acid sequence, e.g., an enzyme, that is not normally present in the host organism and can be expressed in the host cell under proper conditions. As such, "heterologous coding sequences" may include one or additional copies of coding sequences that are not normally present in the host cell, such that the cell is expressing additional copies of a coding sequence that are not normally present in the cells. The heterologous coding sequences can be RNA or any type thereof, e.g., mRNA, DNA or any type thereof, e.g., cDNA, or a hybrid of RNA/DNA. Examples of coding sequences include, but are not limited to, full-length transcription units that comprise such features as the coding sequence, introns, promoter regions, 5'-UTRs, 3'-UTRs and enhancer regions.

"Heterologous coding sequences" also includes the coding portion of the peptide or enzyme, i.e., the cDNA or mRNA sequence, of the peptide or enzyme, as well as the coding portion of the full-length transcriptional unit, i.e., the gene comprising introns and exons, as well as "codon optimized" sequences, truncated sequences or other forms of altered sequences that code for the enzyme or code for its equivalent amino acid sequence, provided that the equivalent amino acid sequence produces a functional protein. Such equivalent amino acid sequences can have a deletion of one or more amino acids, with the deletion being N-terminal, C-terminal or internal. Truncated forms are envisioned as long as they have the catalytic capability indicated herein.

As used herein, the term "control" refers to a sample used in an analytical procedure for comparison purposes. A control can be "positive" or "negative". For example, where the purpose of an analytical procedure is to detect a differentially expressed transcript or polypeptide in cells or tissue, it is generally preferable to include a positive control, such as a sample from a known plant exhibiting the desired expression, and a negative control, such as a sample from a known plant lacking the desired expression.

As used herein, the term "plant" includes a whole plant and any descendant, cell, tissue, or part of a plant. A class of plant that can be used in the present invention is generally as broad as the class of higher and lower plants amenable to mutagenesis including angiosperms (monocotyledonous and dicotyledonous plants), gymnosperms, ferns and multicellular algae. Thus, "plant" includes dicot and monocot plants. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks. In an embodiment, plant material includes root tissues and other plant tissues located underground.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant, comprising a protoplast and a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein.

The term "protoplast," as used herein, refers to a plant cell that had its cell wall completely or partially removed, with the lipid bilayer membrane thereof naked, and thus includes protoplasts, which have their cell wall entirely removed, and spheroplasts, which have their cell wall only partially removed, but is not limited thereto. Typically, a protoplast is an isolated plant cell without cell walls which has the potency for regeneration into cell culture or a whole plant.

Unless otherwise specifically explained, all technical and scientific terms used herein have the same meaning as commonly understood by those of ordinary skill in the art that this disclosure belongs. Definitions of common terms in molecular biology can be found in, for example: Lewin, Genes V, Oxford University Press, 1994; Kendrew et al. (eds.), The Encyclopedia of Molecular Biology, Blackwell Science Ltd., 1994; and Meyers (ed.), Molecular Biology and Biotechnology: A Comprehensive Desk Reference, VCH Publishers, Inc., 1995.

EMBODIMENTS

As disclosed herein, novel recombinant constructs are provided for expressing a transgene using the regulatory sequences of a *Zea mays* metallothionein-like gene. These constructs can be used to transform cells, including plant cells, to produce complete organisms that express the transgene gene product in their cells.

Regulatory Elements

Plant promoters used for basic research or biotechnological applications are generally unidirectional, directing only one gene that has been fused at its 3' end (downstream). It is often necessary to introduce multiple genes into plants for metabolic engineering and trait stacking and therefore, multiple novel promoters are typically required in transgenic crops to drive the expression of multiple genes.

Development of transgenic products is becoming increasingly complex, that requires stacking multiple transgenes into a single locus. Traditionally, each transgene usually requires a unique promoter for expression wherein multiple promoters are required to express different transgenes within one gene stack. This frequently leads to repetitive use of the same promoter within one transgene stack to obtain similar levels of expression patterns of different transgenes for expression of a single polygenic trait. Multi-gene constructs driven by the same promoter are known to cause gene silencing resulting in less efficacious transgenic products in the field. Excess of transcription factor (TF)-binding sites due to promoter repetition can cause depletion of endogenous TFs leading to transcriptional inactivation. The silencing of transgenes will likely undesirably affect performance of a transgenic plant produced to express transgenes. Repetitive sequences within a transgene may lead to gene intra locus homologous recombination resulting in polynucleotide rearrangements.

Provided are methods and constructs using *Zea mays* metallothionein-like gene regulatory elements to express transgenes in plant. In an embodiment, a promoter can be a *Zea mays* metallothionein-like promoter of:

(SEQ ID NO: 1)
ACCATATCATGTCTCAAGCCTTAATACACTTTTAAATAAAT

TTAAATCATTTAATAGAAACTAATTACATGTTAATACATCACTATAAAAA

AAATTAATGGTTGCACCGTAAAGCTTTAACTTGTGCATCTATACTCTAAT

AGTTTGTGGTCCAACGCCTCGGTCCGACATCTATAGAAGTCTTTTTTTCT

TTATTATTTGGTTTCTTTGTGAGCTTCACGTTCAGTTTGGCCCTATTTGT

ACTCTTGCATATACTTATAGATATGTAACATGTTTTCTAACATCTTGCTT

GAGATGTTATTCATTCGAAGCATCCCTTTGTCTAAGTCCACTTGTGCACC

CTTTGAAAAAATGTTAGCATAAATGATTGTGTTAACCATCAAAACACCAA

AACTTTATTTTAAACGGACCTAAGTCTATTTTACTTGCAATGAGCTAGCA

TGAGGAACATGGAGCAACATTAAACTCGAAACAGGAGGCAGTATCAAATA

CTCCCTCTGTTTCTTTTTATTAGTCGCTGGATAGTGAAATTTTGCACTAT

CCAGCGACTAATAAAAAGAAACGGAGGGAGTATGAGAGTCGATCTTAAGA

ACATGACGTATGATCCATACCCTCAAATCTGTTTGAGAAAAATCACTATC

GAAGGAGGCTACTTGTTTTCTTCTTTGCGTAGAAGATAATACTCCTCCTG

TCCTAAATTAATATTTGTTTAAACTTTTTACTAAATTCATGTAATAATTA

ATGTATGCGTTATATATATATGTCTAGGTTTATAATTATTCATATGAATA

TGAACATAAAAATCTAGGGCTAAAACGACTACTATTTTGAAAACGGAAGG

AGTAGTAAGTTATTTAAGCGGAGGGGAACCATGATGGGCTAGTGATTTAA

TTTACATATATATATTGGTGTTCTGGGCTCTTACATGAGAAGATCTAGTT

AACTGTTGTTACTGAACAGCGAAGACAAATATATAATTTAAGCTCCCCAA

CTGCTAGTGATTCTGTTAAGAGGTAATGTTTAAAGTAAATTTACAAGAGC

CCGTCTAGCTCAGTCGGTAGAGCGCAAGGCTCTTAACCTTGTGGTCGTGG

GTTCGAGCCCCACGGTGGGCGCACAATTTTTTGTTTTTTGACATTTTTTG

TTTGCTTAGTTGCAGACGGTTTTTCCCCTGCTAGGAGATTTCCGAGAGAA

AAAAAGGCACTACAGGTTAACCAAAACCACCAACCTTTGGAGCGTCGAG

GCGACGGGCATTTGCGTAGTTGAAGCTTACAAAGTTGCATATGAGATGAG

TGCCGGACATGAAGCGGATAACGTTTTAAACTGGCAACAATATCTAGCTG

TTTCAAATTCAGGCGTGGGAAGCTACGCCTACGCGCCCTGGACGGCGTGT

AAAGAGCCAGCATCGGCATCATTGTCAAACGATCGACAAGGCCAAGAAAT

TCCAAATATATTATTAATAAAAAAGAAGGCACAAATTAGTTTGGTTTTTT

AGTATGTGTGGCGGAGGAAATTTTGAGAACGAACGTATCAAAGAAGGCAC

AAGACGATATAGATTGACGCGGCTAGAAGTTGCAGCAAGACAGTGGGTAC

GGTCTTATATATCCTAATAAATAAAAAATAAAACTATAGTGTGTCAAATG

TCAACAAGAGGAGGAGGCAGCCAAATTAGCAGAGGGAGACAAGTAGAGCA

CGCCTTATTAGCTTGCTTATTTATCGTGGTGGTGTACTTGTTAATTACTG

GCACGCATTATCAACAACGCAGTTCTGGATGTGAATCTAGACAAACATTT

GTCTAGGTTCCGCACGTATAGTTTTTTTTCTTTTTTTTTGGGGGGGGG

TGGGGGGGGGGGGGAACGGAAGCTGTAATAAACGGTACTAGGAACGAAAG

CAACCGCCGCGCGCATGTTTTTGCAATAGATTACGGTGACCTTGATGCAC

CACCGCGTGCTATAAAACCAGTGTCCCCGAGTCTACTCATCAACCAATC

CATAACTCGAAACCTTTTCTTGTGCTCTGTTCTGTCTGTGTTTCCAAA

GCAAACGAAAGAGGTCGAGG

In an embodiment, a promoter can be a truncation of a *Zea mays* metallothionein-like promoter of:

(SEQ ID NO: 2)
TTTAACTTGTGCATCTATACTCTAATAGTTTGTGGTCCAAC

GCCTCGGTCCGACATCTATAGAAGTCTTTTTTTCTTTATTTTGGTTTC

TTTGTGAGCTTCACGTTCAGTTTGGCCCTATTTGTACTCTTGCATATACT

TATAGATATGTAACATGTTTTCTAACATCTTGCTTGAGATGTTATTCATT

CGAAGCATCCCTTTGTCTAAGTCCACTTGTGCACCCTTTGAGCTAGCATG

AGGAACATGGAGCAACATTAAACTCGAAACAGGAGGCAGTATCAAATGAG

AGTCGATCTTAAGAACATGACGTATGATCCATACCCTCAAATCTGTTTGA

GAAAAATCACTATCGAAGGAGGCTACTTGTTTTCTTCTTTGCGTAGAAGA

TAAGTAAGTTATTTAAGCGGAGGGGAACCATGATGGGCTAGTGATTTAAT

TTACATATATATATTGGTGTTCTGGGCTCTTACATGAGAAGATCTAGTTA

ACTGTTGTTACTGAACAGCGAAGACAAATATATAATTTAAGCTCCCCAAC

TGCTAGTGATTCTGTTAAGAGGTAATGTTTAAAGTAAATTGCTTAGTTGC

AGACGGTTTTCCCCTGCTAGGAGATTTCCGAGAGAAAAAAAAGGCACTA

CAGGTTAACCAAAACCACCAACCTTTGGAGCGTCGAGGCGACGGGCATTT

GCGTAGTTGAAGCTTACAAAGTTGCATATGAGATGAGTGCCGGACATGAA

GCGGATAACGTTTTAAACTGGCAACAATATCTAGCTGTTTCAAATTCAGG

CGTGGGAAGCTACGCCTACGCGCCCTGGACGGCGTGTAAAGAGCCAGCAT

CGGCATCATTGTCAAACGATCGACAAGGCCAAGAAATTCCAAATATATTA

TTAATAAAAAAGAAGGCACAAATTAGTTTGGTTTTTTAGTATGTGTGGCG

-continued
```
GAGGAAATTTTGAGAACGAACGTATCAAAGAAGGCACAAGACGATATAGA

TTGACGCGGCTAGAAGTTGCAGCAAGACAGTGGGTACGGTCTTATATATC

CTAATAAATAAAAAATAAAACTATAGTGTGTCAAATGTCAACAAGAGGAG

GAGGCAGCCAAATTAGCAGAGGGAGACAAGTAGAGCACGCCTTATTAGCT

TGCTTATTTATCGTGGTGGTGTACTTGTTAATTACTGGCACGCATTATCA

ACAACGCAGTTCTGGATGTGAATCTAGACAAACATTTGTCTAGGTTCCGC

ACGTATAGTTTTTTTTCTTTTTTTTTGGGGGGGGGTGGGGGGGGGGGG

GAACGGAAGCTGTAATAAACGGTACTAGGAACGAAAGCAACCGCCGCG

CATGTTTTTGCAATAGATTACGGTGACCTTGATGCACCACCGCGTGCTAT

AAAAACCAGTGTCCCCGAGTCTACTCATCAACCAATCCATAACTCGAAAC

CTTTTCTTGTGCTCTGTTCTGTCTGTGTTTCCAAAGCAAACGAAAGAG

GTCGAGG
```

In an embodiment, a nucleic acid construct is provided comprising a promoter. In an embodiment, the promoter is a *Zea mays* metallothionein-like gene promoter. In an embodiment, a nucleic acid construct is provided comprising a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1 or SEQ ID NO:2. In an embodiment, a nucleic acid construct is provided comprising a *Zea mays* metallothionein-like gene promoter that is operably linked to a polylinker. In an embodiment, a gene expression cassette comprises a *Zea mays* metallothionein-like gene promoter that is operably linked to a transgene. In one embodiment the promoter consists of SEQ ID NO:1 or SEQ ID NO:2. In an illustrative embodiment, a gene expression cassette is provided comprising a *Zea mays* metallothionein-like gene promoter that is operably linked to the 5' end of a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In addition to a promoter, a 3'-untranslated gene region (i.e., 3'-UTR) or terminator is needed for transcription, termination and polyadenylation of the mRNA. Proper transcription termination and polyadenylation of mRNA is important for stable expression of transgene. The transcription termination becomes more critical for multigene stacks to avoid transcription read-through into next transgene. Similarly, non-polyadenylated aberrant RNA (aRNA) is a substrate for plant RNA-dependent RNA polymerases (RdRPs) to convert aRNA into double stranded RNA (dsRNA) leading to small RNA production and transgene silencing. Strong transcription terminators therefore are very useful both for single gene and multiple gene stacks. While a promoter is necessary to drive transcription, a 3'-UTR gene region can terminate transcription and initiate polyadenylation of a resulting mRNA transcript for translation and protein synthesis. A 3'-UTR gene region aids stable expression of a transgene.

In accordance with one embodiment, a nucleic acid construct is provided comprising a transcription terminator. In an embodiment, the transcription terminator is a *Zea mays* metallothionein-like gene transcription terminator. In an embodiment, a nucleic acid construct is provided comprising a transcription terminator, wherein the transcription terminator is at least 80%, 85%, 90%, 91%, 92%, 93%, 94%, 95%, 96%, 97%, 98%, 99%, 99.5%, 99.8%, or 100% identical to SEQ ID NO: 3 or SEQ ID NO:4. In an embodiment, a nucleic acid construct is provided comprising a transcription terminator that is operably linked to a polylinker. In an embodiment, a gene expression cassette is provided comprising a transcription terminator that is operably linked to the 3' end of a transgene. In one embodiment, the transcription terminator consists of SEQ ID NO: 3 or SEQ ID NO:4. In an illustrative embodiment, a gene expression cassette comprises a transcription terminator that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof. In one embodiment, a nucleic acid vector is provided comprising a transcription terminator operably linked to either a polylinker sequence, a transgene, or a combination of both. In one embodiment, the transcription terminator is less than 1 kb in length.

In an embodiment, a nucleic acid construct is provided comprising a promoter as described herein and a 3'-UTR. In an embodiment, the nucleic acid construct comprises a 3'-UTR. In an embodiment, the 3'-UTR is a *Zea mays* metallothionein-like 3'-UTR.

In an embodiment, a 3'-UTR can be a *Zea mays* metallothionein-like 3'-UTR of:

(SEQ ID NO: 3)
```
TCCTGCTGCGTTGTTTCGTTTGCGGCATGCATGGATGTCAC

CTTTTTTTTACTGTCTGCTTTGTGCTTGTGGCGTGTCAAGAATAAAGGAT

GGAGCCATCGTCTGGTCTGACTCTGGCTCTCCGCCATGCATGCTTGGTGT

CGGTTCTGTTGTGCTTGTGTTGGTGCATGTAATCGTATGGCATCGTTACA

CACCATGCATCTCTGATCTCTTTGCGCCAGTGTGTGTGACTATGTCCCTG

TAACGATTGGCTCAGTGATTGAATATATATACAATACTGTTTTACTAAGT

AAGTATGATTACCTCTTATTTTAAATTTCTCTATGTAAATCATGTCTTCT

ACACAGTATGTTGTACGACCACTATCTGCTGAATGTATAGATGTCTAGAA

AGCACGTGGCCCGTTAGCATGACACGAAGCACGGTTTTTTAGCACGACAC

AAATTAACATGGGCCCAGGCTCAGCCCGGCCCAGCGAGCGTGTCGGGCTC

GACAGCCATCCCGACGCGTTGGGCTGGCCCGAGCACGGCCCGGTGGATGT

TGGGCTTAGAAACCGGCCCGCTACATTTTAGCGCAGCCTAACCCACTGCC

CACCAATACTCCGCAATTCCGCATAAATCCCCCAGTGCCCCATCCCCAGC

CCATTGACCAGCGCGACAGCTAGGGCTGGAAAAAAAGCTCGAGGCTCGCG

AGCCAGCTCGGGCTCGATCAGGCTCGGCTCGGCTCGGTGAGGCTCGCGAG

CCTAAACGAGCCCGAGCCGAGCCTAATTCCGCAGCTCGCTACACTAACGA

GCCGAGCCGGCTTGGTGAGGCTCGCGAGCGGGCTCAAGGCTTGGTCCAAA

CTACTACTTACTCGTATCTCCGTTCACCAGTGTGTAAGTGTGCTGTTTTG

GTCACAACTCACAAGGAACTAGAGTGCAGGGACATAATTTTTTATTATAT

GGAACATATTGTGCTTCAAATTTGAGCTAATGACTATAATTATTGTTGTT

GAGTACTTGAGTGTACAGGCTCGCGAGCCTATATCGAGCCGAGCCTCATT

ACCGAGCTCGCTAAGTGACCGAGCCGAGCCTGGCTCGGC
```

In an embodiment, a 3'-UTR can be a truncation of a *Zea mays* metallothionein-like 3'-UTR of:

```
                                           (SEQ ID NO: 4)
       TCCTGCTGCGTTGTTTCGTTTGCGGCATGCATGGATGTCA

CCTTTTTTTTACTGTCTGCTTTGTGCTTGTGGCGTGTCAAGAATAAAGGA

TGGAGCCATCGTCTGGTCTGACTCTGGCTCTCCGCCATGCATGCTTGGTG

TCGGTTCTGTTGTGCTTGTGTTGGTGCATGTAATCGTATGGCATCGTTAC

ACACCATGCATCTCTGATCTCTTTGCGCCAGTGTGTGTGACTATGTCCCT

GTAACGATTGGCTCAGTGATTGAATATATATACAATACTGTTTTACTAAG

TAAGTATGATTACCTCTTATTTTAAATTTCTCTATGTAAATCATGTCTTC

TACACAGTATGTTGTACGACCACTATCTGCTGAATG
```

In an embodiment, a nucleic acid construct is provided comprising a promoter as described herein and a 3'-UTR. In an embodiment, a 3'-UTR can be a *Zea mays* metallothionein-like gene 3'-UTR. In an embodiment, the 3'-UTR is at least 80%, 85%, 90%, 91%, 92%, 93%, 94%, 95%, 96%, 97%, 98%, 99%, 99.5%, 99.8%, or 100% identical to SEQ ID NO:3 or SEQ ID NO:4. In an embodiment, nucleic acid construct is provided comprising a promoter as described herein and the 3'-UTR wherein the promoter and 3'-UTR are both operably linked to opposite ends of a polylinker. In an embodiment, a gene expression cassette is provided comprising a promoter as described herein and a 3'-UTR, wherein the promoter and 3'-UTR are both operably linked to opposite ends of a transgene. In one embodiment the 3'-UTR consists of SEQ ID NO:3 or SEQ ID NO:4. In one embodiment, a gene expression cassette is provided comprising a promoter as described herein and a 3'-UTR. In one embodiment the promoter consists of SEQ ID NO: 1 or SEQ ID NO: 2 and the 3'-UTR consists of SEQ ID NO:3 or SEQ ID NO: 4.

In an illustrative embodiment, a gene expression cassette comprises a *Zea mays* metallothionein-like gene 3'-UTR that is operably linked to a transgene. In an illustrative embodiment, a gene expression cassette comprises a 3'-UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof. In a further embodiment, the transgene is operably linked to a promoter and a 3'-UTR from the same *Zea mays* metallothionein-like gene.

In an embodiment, a nucleic acid construct is provided comprising a promoter as described herein and a 5'-UTR. In one embodiment, the intron is operably linked to the promoter. In an embodiment, a nucleic acid construct is provided comprising an intron operably linked to a promoter isolated from a maize gene encoding a *Zea mays* metallothionein-like protein or a derivative of such promoter sequence. In an embodiment, the 5'-UTR can be a *Zea mays* metallothionein-like 5'-UTR of:

```
                                           (SEQ ID NO: 5)
       ATCAACCAATCCATAACTCGAAACCTTTTCTTGTGCTCTGT

TCTGTCTGTGTGTTTCCAAAGCAAACGAAAGAGGTCGAGG
```

In an embodiment, a nucleic acid construct is provided comprising a promoter as described herein and a 5'-UTR, wherein the 5'-UTR is at least 80%, 85%, 90%, 91%, 92%, 93%, 94%, 95%, 96%, 97%, 98%, 99%, 99.5%, 99.8%, or 100% identical to SEQ ID NO:5. In an embodiment, a nucleic acid construct is provided comprising a promoter as described herein, a 5'-UTR sequence and a polylinker wherein the promoter and 5'-UTR are operably linked to a polylinker. In an embodiment, a gene expression cassette is provided comprising a promoter as described herein, a 5'-UTR sequence, and a transgene wherein the promoter and 5'-UTR are operably linked to the 5' end of the transgene. Optionally the construct further comprises a 3'-UTR that is operably linked to the 3' end of the transgene or polylinker. In one embodiment the promoter and 3'-UTR sequences are selected from those described herein and the 5'-UTR sequence consists of SEQ ID NO:5. In an embodiment, a gene expression cassette comprises a 5'-UTR from a maize gene encoding a *Zea mays* metallothionein-like protein that is operably linked to a promoter, wherein the promoter is a *Zea mays* metallothionein-like gene promoter, or a promoter that originates from a plant (e.g., *Zea mays* ubiquitin 1 promoter), a virus (e.g., Cassava vein mosaic virus promoter) or a bacteria (e.g., *Agrobacterium tumefaciens* delta mas). In an illustrative embodiment, a gene expression cassette comprises a 5'-UTR from a maize gene encoding a *Zea mays* metallothionein-like protein that is operably linked to a transgene, wherein the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof.

In one embodiment, a nucleic acid construct is provided comprising a promoter and a polylinker and optionally one or more of the following elements:
a) a 5' untranslated region; and
b) a 3' untranslated region,
wherein
  the promoter consists of SEQ ID NO:1 or SEQ ID NO:2 or a sequence having 98% sequence identity with SEQ ID NO:1 or SEQ ID NO:2;
  the 5' untranslated region consists of SEQ ID NO:5 or a sequence having 98% sequence identity with SEQ ID NO:5; and
  the 3' untranslated region consists of SEQ ID NO:3 or SEQ ID NO:4 or a sequence having 98% sequence identity with SEQ ID NO:3 or SEQ ID NO:4; further wherein said promoter is operably linked to said polylinker and each optional element, when present, is also operably linked to both the promoter and the polylinker.

In one embodiment, a nucleic acid construct is provided comprising a promoter and a transgene and optionally one or more of the following elements:
a) a 5' untranslated region; and
b) a 3' untranslated region,
wherein
  the promoter consists of SEQ ID NO:1 or SEQ ID NO:2 or a sequence having 98% sequence identity with SEQ ID NO:1 or SEQ ID NO:2;
  the 5' untranslated region consists of SEQ ID NO:5 or a sequence having 98% sequence identity with SEQ ID NO:5; and
  the 3' untranslated region consists of SEQ ID NO:3 or SEQ ID NO:4 or a sequence having 98% sequence identity with SEQ ID NO:3 or SEQ ID NO:4; further wherein said promoter is operably linked to said transgene and each optional element, when present, is also operably linked to both the promoter and the transgene. In a further embodiment a transgenic cell is provided comprising the nucleic acid construct disclosed immediately above. In one embodiment the transgenic cell is a plant cell, and in a further embodiment a plant is provided wherein the plant comprises said transgenic cells.

In an embodiment, a gene expression cassette comprises a Zea mays metallothionein-like promoter, a Zea mays metallothionein-like 5'-UTR, and a Zea mays metallothionein-like 3'-UTR. In an embodiment, a gene expression cassette comprises: a) a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1 or SEQ ID NO:2; b) a 5'-UTR, wherein the 5'-UTR is at least 80%, 85%, 90%, 91%, 92%, 93%, 94%, 95%, 96%, 97%, 98%, 99%, 99.5%, 99.8%, or 100% identical to SEQ ID NO:5; and, c) a 3'-UTR, wherein the 3'-UTR is at least 80%, 85%, 90%, 91%, 92%, 93%, 94%, 95%, 96%, 97%, 98%, 99%, 99.5%, 99.8%, or 100% identical to SEQ ID NO:3 or SEQ ID NO:4.

For example, a gene expression cassette may include both a promoter, a 5'-UTR, and a 3'-UTR wherein the promoter is a polynucleotide of SEQ ID NO:1, the 5'-UTR is a polynucleotide of SEQ ID NO:5, and the 3'-UTR is a polynucleotide of SEQ ID NO:3. Likewise, a gene expression cassette may include a promoter, a 5'-UTR, and a 3'-UTR wherein the promoter is a polynucleotide of SEQ ID NO:2, the 5'-UTR is a polynucleotide of SEQ ID NO:5, and the 3'-UTR is a polynucleotide of SEQ ID NO:4. Furthermore, a gene expression cassette may include a promoter, a 5'-UTR, and a 3'-UTR wherein the promoter is a polynucleotide of SEQ ID NO:2, the 5'-UTR is a polynucleotide of SEQ ID NO:5, and the 3'-UTR is a polynucleotide of SEQ ID NO:3. In addition, a gene expression cassette may include a promoter, a 5'-UTR, and a 3'-UTR wherein the promoter is a polynucleotide of SEQ ID NO:1, the 5'-UTR is a polynucleotide of SEQ ID NO:5, and the 3'-UTR is a polynucleotide of SEQ ID NO:4.

In an embodiment, a gene expression cassette comprises a Zea mays metallothionein-like promoter, a Zea mays metallothionein-like 5'-UTR, and a Zea mays metallothionein-like 3'-UTR that are operably linked to a transgene or a heterologous coding sequence. A promoter, a 5'-UTR, and 3'-UTR can be operably linked to different transgenes within a gene expression cassette when a gene expression cassette includes one or more transgenes. In an illustrative embodiment, a gene expression cassette comprises a Zea mays metallothionein-like promoter that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof. In an illustrative embodiment, a gene expression cassette comprises a Zea mays metallothionein-like promoter, a Zea mays metallothionein-like 5'-UTR, and a Zea mays metallothionein-like 3'-UTR that are operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof. In an illustrative embodiment, a gene expression cassette comprises a Zea mays metallothionein-like 3'-UTR that is operably linked to a transgene, wherein the transgene encodes for a gene product that enhances insecticidal resistance, herbicide tolerance, nitrogen use efficiency, water use efficiency, nutritional quality, or combinations thereof.

A Zea mays metallothionein-like 5'-UTR and a Zea mays metallothionein-like 3'-UTR can be operably linked to different promoters within a gene expression cassette. In an illustrative embodiment, promoters originate from a plant (e.g., Zea mays ubiquitin 1 promoter), a virus (e.g., Cassava vein mosaic virus promoter) or a bacteria (e.g., Agrobacterium tumefaciens delta mas). In a further embodiment, the gene expression cassette comprises a promoter that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In an embodiment, a vector comprises a gene expression cassette as disclosed herein. In an embodiment, a vector can be a plasmid, a cosmid, a bacterial artificial chromosome (BAC), a bacteriophage, a virus, or an excised polynucleotide fragment for use in transformation or gene targeting such as a donor DNA.

In accordance with one embodiment, a nucleic acid vector is provided comprising a recombinant gene cassette wherein the recombinant gene cassette comprises a promoter operably linked to a polylinker sequence, a transgene, or combination thereof. In one embodiment the recombinant gene cassette comprises a promoter operably linked to a transgene. In one embodiment the recombinant gene cassette comprises a promoter as disclosed herein operably linked to a polylinker sequence. The polylinker is operably linked to the promoter in a manner such that insertion of a coding sequence into one of the restriction sites of the polylinker will operably link the coding sequence allowing for expression of the coding sequence when the vector is transfected into a host cell.

In accordance with one embodiment the promoter comprises SEQ ID NO:1 or a sequence that has 90, 95 or 99% sequence identity with SEQ ID NO:1. In accordance with one embodiment the promoter sequence has a total length of no more than 1.5, 2, 2.5, 3 or 4 kb. In accordance with one embodiment the promoter consists of SEQ ID NO:1 or a 2061 bp sequence that has 90, 95 or 99% sequence identity with SEQ ID NO:1.

In accordance with one embodiment the promoter comprises SEQ ID NO:2 or a sequence that has 90, 95 or 99% sequence identity with SEQ ID NO:2. In accordance with one embodiment the promoter sequence has a total length of no more than 1.5, 2, 2.5, 3 or 4 kb. In accordance with one embodiment the promoter consists of SEQ ID NO:2 or a 1498 bp sequence that has 90, 95 or 99% sequence identity with SEQ ID NO:2.

In accordance with one embodiment a nucleic acid vector is provided comprising a gene cassette that consists of SEQ ID NO:1, a transgene and a 3'-UTR, wherein SEQ ID NO:1 is operably linked to the 5' end of the transgene and the 3'-UTR is operably linked to the 3' end of the transgene. In a further embodiment the 3' untranslated sequence comprises SEQ ID NO:3 or a sequence that has 90, 95, 99 or 100% sequence identity with SEQ ID NO:3. In accordance with one embodiment a nucleic acid vector is provided comprising a gene cassette that consists of SEQ ID NO:1, or a 2061 bp sequence that has 90, 95, or 99% sequence identity with SEQ ID NO:1, a transgene and a 3'-UTR, wherein SEQ ID NO:1 is operably linked to the 5' end of the transgene and the 3'-UTR is operably linked to the 3' end of the transgene. In a further embodiment the 3' untranslated sequence comprises SEQ ID NO:3 or a sequence that has 90, 95, 99 or 100% sequence identity with SEQ ID NO:3. In a further embodiment the 3' untranslated sequence consists of SEQ ID NO:3, or a 1080 bp sequence that has 90, 95, or 99% sequence identity with SEQ ID NO:3.

In accordance with one embodiment a nucleic acid vector is provided comprising a gene cassette that consists of SEQ ID NO:2, a transgene and a 3'-UTR, wherein SEQ ID NO:2 is operably linked to the 5' end of the transgene and the 3'-UTR is operably linked to the 3' end of the transgene. In a further embodiment the 3' untranslated sequence comprises SEQ ID NO:4 or a sequence that has 90, 95, 99 or 100% sequence identity with SEQ ID NO:4. In accordance with one embodiment a nucleic acid vector is provided comprising a gene cassette that consists of SEQ ID NO:2, or a 1498 bp sequence that has 90, 95, or 99% sequence identity with SEQ ID NO:2, a transgene and a 3'-UTR, wherein SEQ ID NO:2 is operably linked to the 5' end of the transgene and the 3'-UTR is operably linked to the 3' end of the transgene. In a further embodiment the 3' untranslated sequence comprises SEQ ID NO:4 or a sequence that has 90, 95, 99 or 100% sequence identity with SEQ ID NO:4. In a further embodiment the 3' untranslated sequence consists of SEQ ID NO:4, or a 376 bp sequence that has 90, 95, or 99% sequence identity with SEQ ID NO:4.

In accordance with one embodiment the nucleic acid vector further comprises a sequence encoding a selectable maker. In accordance with one embodiment the recombinant gene cassette is operably linked to an *Agrobacterium* T-DNA border. In accordance with one embodiment the recombinant gene cassette further comprises a first and second T-DNA border, wherein first T-DNA border is operably linked to one end of the gene construct, and said second T-DNA border is operably linked to the other end of the gene construct. The first and second *Agrobacterium* T-DNA borders can be independently selected from T-DNA border sequences originating from bacterial strains selected from the group consisting of a nopaline synthesizing *Agrobacterium* T-DNA border, an ocotopine synthesizing *Agrobacterium* T-DNA border, a succinamopine synthesizing *Agrobacterium* T-DNA border, or any combination thereof. In one embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene operably linked to a sequence selected from SEQ ID NO:1, SEQ ID NO:2 or a sequence having 90, 95, or 99% sequence identity with SEQ ID NO:1 or SEQ ID NO:2.

Transgenes of interest and suitable for use in the present disclosed constructs include, but are not limited to, coding sequences that confer (1) resistance to pests or disease, (2) resistance to herbicides, and (3) value added traits as disclosed in WO2013116700 (DGT-28), US20110107455 (DSM-2), U.S. Pat. No. 8,283,522 (AAD-12); U.S. Pat. No. 7,838,733 (AAD-1); U.S. Pat. Nos. 5,188,960; 5,691,308; 6,096,708; and 6,573,240 (Cry1F); U.S. Pat. Nos. 6,114,138; 5,710,020; and 6,251,656 (Cry1Ac); U.S. Pat. Nos. 6,127,180; 6,624,145 and 6,340,593 (Cry34Ab1); U.S. Pat. Nos. 6,083,499; 6,548,291 and 6,340,593 (Cry35Ab1), the disclosures of which are incorporated herein. In accordance with one embodiment the transgene encodes a selectable marker or a gene product conferring insecticidal resistance, herbicide tolerance, nitrogen use efficiency, water use efficiency, or nutritional quality.

In accordance with one embodiment a nucleic acid vector is provided comprising a gene cassette wherein the gene cassette comprises a promoter region operably linked to the 5' end of a transgene wherein the 3' end of the transgene is linked to a 3' untranslated region. In one embodiment the promoter region comprises SEQ ID NO:1 or a sequence that has 90, 95 or 99% sequence identity with SEQ ID NO:1. In another embodiment the promoter region comprises SEQ ID NO:2 or a sequence that has 90, 95 or 99% sequence identity with SEQ ID NO:2. In accordance with one embodiment the promoter region consists of SEQ ID NO:1 or SEQ ID NO:2. In one embodiment the 3' untranslated sequence comprises SEQ ID NO:3 or a sequence that has 90, 95 or 99% sequence identity with SEQ ID NO:3, and in one embodiment the 3' untranslated sequence consists of SEQ ID NO:3 or a 1080 bp sequence having 90, 95 or 99% sequence identity with SEQ ID NO:3. In another embodiment the 3' untranslated sequence comprises SEQ ID NO:4 or a sequence that has 90, 95 or 99% sequence identity with SEQ ID NO:4, and in one embodiment the 3' untranslated sequence consists of SEQ ID NO:4 or a 376 bp sequence having 90, 95 or 99% sequence identity with SEQ ID NO:4.

In accordance with one embodiment a nucleic acid vector is provided comprising a gene cassette wherein the gene cassette comprises a promoter region operably linked to the 5' end of a 5' untranslated sequence, wherein the 3' end of the 5' untranslated sequence is operably linked to the 5' end of the transgene wherein the 3' end of the transgene is linked to a 3' untranslated region. In one embodiment the promoter region comprises or consists of SEQ ID NO:1 or a sequence that has 90, 95 or 99% sequence identity with SEQ ID NO:1. In one embodiment the promoter region consists of SEQ ID NO:1 or a 2061 bp sequence that has 90, 95 or 99% sequence identity with SEQ ID NO:1. In one embodiment the promoter region comprises or consists of SEQ ID NO:2 or a sequence that has 90, 95 or 99% sequence identity with SEQ ID NO:2. In one embodiment the promoter region consists of SEQ ID NO:2 or a 1498 by sequence that has 90, 95 or 99% sequence identity with SEQ ID NO:2. In accordance with one embodiment the 5' untranslated sequence comprises or consists of SEQ ID NO:5 or a sequence that has 90% sequence identity with SEQ ID NO:5. In accordance with one embodiment the 5' untranslated sequence consists of SEQ ID NO:5 or a 84 bp sequence that has 90% sequence identity with SEQ ID NO:5. In one embodiment the 3' untranslated sequence comprises or consists of SEQ ID NO:3 or a sequence that has 90, 95 or 99% sequence identity with SEQ ID NO:3. In one embodiment the 3' untranslated sequence consists of SEQ ID NO:3 or a 1080 bp sequence that has 90, 95 or 99% sequence identity with SEQ ID NO:3. In one embodiment the 3' untranslated sequence comprises or consists of SEQ ID NO:4 or a sequence that has 90, 95 or 99% sequence identity with SEQ ID NO:4. In one embodiment the 3' untranslated sequence consists of SEQ ID NO:4 or a 376 bp sequence that has 90, 95 or 99% sequence identity with SEQ ID NO:4.

In accordance with one embodiment a nucleic acid vector is provided comprising a gene cassette wherein the gene cassette comprises a promoter region operably linked to the 5' end of a transgene wherein the 3' end of the transgene is linked to a 3' untranslated region. In one embodiment the promoter region comprises SEQ ID NO:1 or a sequence that has 90, 95 or 99% sequence identity with SEQ ID NO:1. In accordance with one embodiment the promoter region consists of SEQ ID NO:1 or a 2061 bp sequence having 90, 95 or 99% sequence identity with SEQ ID NO:1. In accordance with one embodiment the promoter region consists of SEQ ID NO:1. In one embodiment the promoter region comprises SEQ ID NO:2 or a sequence that has 90, 95 or 99% sequence identity with SEQ ID NO:2. In accordance with one embodiment the promoter region consists of SEQ ID NO:2 or a 1498 bp sequence having 90, 95 or 99% sequence identity with SEQ ID NO:2. In accordance with one embodiment the promoter region consists of SEQ ID NO:2. In one embodiment the 3' untranslated sequence consists of SEQ ID NO:3 or a 1080 bp sequence that has 90, 95 or 99% sequence identity with SEQ ID NO:3, and in one embodiment the 3' untranslated sequence consists of SEQ ID NO:3. In one embodiment the 3' untranslated sequence consists of SEQ ID NO:4 or a 376 bp sequence that has 90, 95 or 99% sequence identity with SEQ ID NO:4, and in one embodiment the 3' untranslated sequence consists of SEQ ID NO:4.

In an embodiment, a cell or plant is provided comprising a gene expression cassette as disclosed herein. In an embodiment, a cell or plant comprises a vector comprising a gene expression cassette as disclosed herein. In an embodiment, a vector can be a plasmid, a cosmid, a bacterial artificial chromosome (BAC), a bacteriophage, or a virus. Thereby, a cell or plant comprising a gene expression cassette as disclosed herein is a transgenic cell or transgenic plant, respectively. In an embodiment, a transgenic plant can be a monocotyledonous plant. In an embodiment, a transgenic monocotyledonous plant can be, but is not limited to maize, wheat, rice, sorghum, oats, rye, bananas, sugar cane, and millet. In an embodiment, a transgenic plant can be a dicotyledonous plant. In an embodiment, a transgenic dicotyledonous plant can be, but is not limited to soybean, cotton, sunflower, and canola. An embodiment also includes a transgenic seed from a transgenic plant as disclosed herein.

In an embodiment, a gene expression cassette includes two or more transgenes. The two or more transgenes may not be operably linked to the same promoter, 5'-UTR, or 3'-UTR as disclosed herein. In an embodiment, a gene expression cassette includes one or more transgenes. In an embodiment with one or more transgenes, at least one transgene is operably linked to a promoter, 5'-UTR, or 3'-UTR of the subject disclosure.

Selectable Markers

Various selectable markers also described as reporter genes can be incorporated into a chosen expression vector to allow for identification and selection of transformed plants ("transformants"). Many methods are available to confirm expression of selectable markers in transformed plants, including for example DNA sequencing and PCR (polymerase chain reaction), Southern blotting, RNA blotting, immunological methods for detection of a protein expressed from the vector, e g., precipitated protein that mediates phosphinothricin resistance, or visual observation of other proteins such as reporter genes encoding β-glucuronidase (GUS), luciferase, green fluorescent protein (GFP), yellow fluorescent protein (YFP), DsRed, β-galactosidase, chloramphenicol acetyltransferase (CAT), alkaline phosphatase, and the like (See Sambrook, et al., Molecular Cloning: A Laboratory Manual, Third Edition, Cold Spring Harbor Press, N.Y., 2001, the content is incorporated herein by reference in its entirety).

Selectable marker genes are utilized for selection of transformed cells or tissues. Selectable marker genes include genes encoding antibiotic resistance, such as those encoding neomycin phosphotransferase II (NEO) and hygromycin phosphotransferase (HPT) as well as genes conferring resistance to herbicidal compounds. Herbicide resistance genes generally code for a modified target protein insensitive to the herbicide or for an enzyme that degrades or detoxifies the herbicide in the plant before it can act. For example, resistance to glyphosate has been obtained by using genes coding for mutant target enzymes, 5-enolpyruvylshikimate-3-phosphate synthase (EPSPS). Genes and mutants for EPSPS are well known, and further described below. Resistance to glufosinate ammonium, bromoxynil, and 2,4-dichlorophenoxyacetate (2,4-D) have been obtained by using bacterial genes encoding pat or DSM-2, a nitrilase, an aad-1 or an aad-12 gene, which detoxifies the respective herbicides.

In an embodiment, herbicides can inhibit the growing point or meristem, including imidazolinone or sulfonylurea, and genes for resistance/tolerance of acetohydroxyacid synthase (AHAS) and acetolactate synthase (ALS) for these herbicides are well known. Glyphosate resistance genes include mutant 5-enolpyruvylshikimate-3-phosphate synthase (EPSPs) and dgt-28 genes (via the introduction of recombinant nucleic acids and/or various forms of in vivo mutagenesis of native EPSPs genes), aroA genes and glyphosate acetyl transferase (GAT) genes, respectively). Resistance genes for other phosphono compounds include bar genes from Streptomyces species, including *Streptomyces hygroscopicus* and *Streptomyces viridichromogenes*, and pyridinoxy or phenoxy proprionic acids and cyclohexones (ACCase inhibitor-encoding genes). Exemplary genes conferring resistance to cyclohexanediones and/or aryloxyphenoxypropanoic acid (including Haloxyfop, Diclofop, Fenoxyprop, Fluazifop, Quizalofop) include genes of acetyl coenzyme A carboxylase (ACCase)—Acc1-S1, Acc1-S2 and Acc1-S3. In an embodiment, herbicides can inhibit photosynthesis, including triazine (psbA and 1s+ genes) or benzonitrile (nitrilase gene).

In an embodiment, selectable marker genes include, but are not limited to genes encoding: neomycin phosphotransferase II; cyanamide hydratase; aspartate kinase; dihydrodipicolinate synthase; tryptophan decarboxylase; dihydrodipicolinate synthase and desensitized aspartate kinase; bar gene; tryptophan decarboxylase; neomycin phosphotransferase (NEO); hygromycin phosphotransferase (HPT or HYG); dihydrofolate reductase (DHFR); phosphinothricin acetyltransferase; 2,2-dichloropropionic acid dehalogenase; acetohydroxyacid synthase; 5-enolpyruvyl-shikimate-phosphate synthase (aroA); haloarylnitrilase; acetyl-coenzyme A carboxylase; dihydropteroate synthase (sul I); and 32 kD photosystem II polypeptide (psbA).

An embodiment also includes genes encoding resistance to: chloramphenicol; methotrexate; hygromycin; spectinomycin; bromoxynil; glyphosate; and phosphinothricin.

The above list of selectable marker genes is not meant to be limiting. Any reporter or selectable marker gene are encompassed by the present invention.

Selectable marker genes are synthesized for optimal expression in a plant. For example, in an embodiment, a coding sequence of a gene has been modified by codon optimization to enhance expression in plants. A selectable marker gene can be optimized for expression in a particular plant species or alternatively can be modified for optimal expression in dicotyledonous or monocotyledonous plants. Plant preferred codons may be determined from the codons of highest frequency in the proteins expressed in the largest amount in the particular plant species of interest. In an embodiment, a selectable marker gene is designed to be expressed in plants at a higher level resulting in higher transformation efficiency. Methods for plant optimization of genes are well known. Guidance regarding the optimization and manufacture of synthetic polynucleotide sequences can be found in, for example, WO2013016546, WO2011146524, WO1997013402, U.S. Pat. No. 6,166,302, and U.S. Pat. No. 5,380,831, herein incorporated by reference.

Transformation

Suitable methods for transformation of plants include any method that DNA can be introduced into a cell, for example and without limitation: electroporation (see, e.g., U.S. Pat. No. 5,384,253); micro-projectile bombardment (see, e.g., U.S. Pat. Nos. 5,015,580; 5,550,318; 5,538,880; 6,160,208; 6,399,861; and 6,403,865); *Agrobacterium*-mediated transformation (see, e.g., U.S. Pat. Nos. 5,635,055; 5,824,877; 5,591,616; 5,981,840; and 6,384,301); and protoplast transformation (see, e.g., U.S. Pat. No. 5,508,184). These methods may be used to stably transform or transiently transform a plant.

A DNA construct may be introduced directly into the genomic DNA of the plant cell using techniques such as agitation with silicon carbide fibers (See, e.g., U.S. Pat. Nos. 5,302,523 and 5,464,765), or the DNA constructs can be introduced directly to plant tissue using biolistic methods, such as DNA particle bombardment (see, e.g., Klein et al., (1987) *Nature* 327:70-73). Alternatively, the DNA construct can be introduced into the plant cell via nanoparticle transformation (see, e.g., U.S. Patent Publication No. 2009/0104700, incorporated herein by reference in its entirety).

In addition, gene transfer may be achieved using non-*Agrobacterium* bacteria or viruses such as *Rhizobium* sp. NGR234, *Sinorhizoboium meliloti, Mesorhizobium loti*, potato virus X, cauliflower mosaic virus and cassava vein mosaic virus and/or tobacco mosaic virus, see, e.g., Chung et al., (2006) *Trends Plant Sci.* 11(1):1-4.

Through the application of transformation techniques, cells of virtually any plant species may be stably transformed, and these cells may be developed into transgenic plants by well-known techniques. For example, techniques that may be particularly useful in the context of cotton transformation are described in U.S. Pat. Nos. 5,846,797; 5,159,135; 5,004,863; and 6,624,344; techniques for transforming *Brassica* plants in particular are described, for example, in U.S. Pat. No. 5,750,871; techniques for transforming soy bean are described, for example, in U.S. Pat. No. 6,384,301; and techniques for transforming maize are described, for example, in U.S. Pat. Nos. 7,060,876 and 5,591,616, and International PCT Publication WO 95/06722.

After effecting delivery of an exogenous nucleic acid to a recipient cell, a transformed cell is generally identified for further culturing and plant regeneration. In order to improve the ability to identify transformants, one may desire to employ a selectable marker gene with the transformation vector used to generate the transformant. In an illustrative embodiment, a transformed cell population can be assayed by exposing the cells to a selective agent or agents, or the cells can be screened for the desired marker gene trait.

Cells that survive exposure to a selective agent, or cells that have been scored positive in a screening assay, may be cultured in media that supports regeneration of plants. In an embodiment, any suitable plant tissue culture media may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

To confirm the presence of a desired nucleic acid comprising constructs provided in regenerating plants, a variety of assays may be performed. Such assays may include: molecular biological assays, such as Southern and Northern blotting and PCR; biochemical assays, such as detecting the presence of a protein product, e.g., by immunological means (ELISA, western blots, and/or LC-MS MS spectrophotometry) or by enzymatic function; plant part assays, such as leaf or root assays; and/or analysis of the phenotype of the whole regenerated plant.

Transgenic events may be screened, for example, by PCR amplification using, e.g., oligonucleotide primers specific for nucleic acid molecules of interest. PCR genotyping is understood to include, but not be limited to, polymerase-chain reaction (PCR) amplification of genomic DNA derived from isolated host plant callus tissue predicted to contain a nucleic acid molecule of interest integrated into the genome, followed by standard cloning and sequence analysis of PCR amplification products. Methods of PCR genotyping have been well described (see, e.g., Rios et al. (2002) Plant J. 32:243-53), and may be applied to genomic DNA derived from any plant species or tissue type, including cell cultures. Combinations of oligonucleotide primers that bind to both target sequence and introduced sequence may be used sequentially or multiplexed in PCR amplification reactions. Oligonucleotide primers designed to anneal to the target site, introduced nucleic acid sequences, and/or combinations of the two may be produced. Thus, PCR genotyping strategies may include, for example and without limitation: amplification of specific sequences in the plant genome; amplification of multiple specific sequences in the plant genome; amplification of non-specific sequences in the plant genome; and combinations of any of the foregoing. One skilled in the art may devise additional combinations of primers and amplification reactions to interrogate the genome. For example, a set of forward and reverse oligonucleotide primers may be designed to anneal to nucleic acid sequence(s) specific for the target outside the boundaries of the introduced nucleic acid sequence.

Forward and reverse oligonucleotide primers may be designed to anneal specifically to an introduced nucleic acid molecule, for example, at a sequence corresponding to a coding region within a nucleotide sequence of interest comprised therein, or other parts of the nucleic acid molecule. Primers may be used in conjunction with primers described herein. Oligonucleotide primers may be synthesized according to a desired sequence and are commercially available (e.g., from Integrated DNA Technologies, Inc., Coralville, Iowa). Amplification may be followed by cloning and sequencing, or by direct sequence analysis of amplification products. In an embodiment, oligonucleotide primers specific for the gene target are employed in PCR amplifications.

Method of Expressing a Transgene

In an embodiment, a method of expressing at least one transgene in a plant comprises growing a plant comprising a *Zea mays* metallothionein-like promoter operably linked to at least one transgene. In an embodiment, a method of expressing at least one transgene in a plant comprising growing a plant comprising a *Zea mays* metallothionein-like 3'-UTR operably linked to at least one transgene. In an embodiment, a method of expressing at least one transgene in a plant comprising growing a plant comprising a *Zea mays* metallothionein-like 5'-UTR operably linked to at least one transgene. In an embodiment, a method of expressing at least one transgene in a plant comprising growing a plant comprising a *Zea mays* metallothionein-like promoter, and/or a *Zea mays* metallothionein-like 3'-UTR, and/or a *Zea mays* metallothionein-like 5'-UTR operably linked to at least one transgene.

In an embodiment, a method of expressing at least one transgene in a plant tissue or plant cell comprising culturing a plant tissue or plant cell comprising a *Zea mays* metallothionein-like promoter operably linked to at least one transgene. In an embodiment, a method of expressing at least one transgene in a plant tissue or plant cell comprising culturing a plant tissue or plant cell comprising a *Zea mays* metallothionein-like 3'-UTR operably linked to at least one transgene. In an embodiment, a method of expressing at least one transgene in a plant tissue or plant cell comprising culturing a plant tissue or plant cell comprising a *Zea mays* metallothionein-like 5'-UTR operably linked to at least one transgene. In an embodiment, a method of expressing at least one transgene in a plant tissue or plant cell comprising culturing a plant tissue or plant cell comprising a *Zea mays* metallothionein-like promoter, and a *Zea mays* metallothionein-like 3'-UTR, and a *Zea mays* metallothionein-like 5'-UTR operably linked to at least one transgene.

In an embodiment, a method of expressing at least one transgene in a plant comprises growing a plant comprising a gene expression cassette comprising a *Zea mays* metallothionein-like promoter operably linked to at least one transgene. In one embodiment the promoter consists of a sequence selected from SEQ ID NO:1 and SEQ ID NO:2 or a sequence that has 90, 95 or 99% sequence identity with a sequence selected from SEQ ID NO:1 and SEQ ID NO:2. In an embodiment, a method of expressing at least one transgene in a plant comprises growing a plant comprising a gene expression cassette comprising a *Zea mays* metallothionein-like 5'-UTR operably linked to at least one transgene. In an embodiment, a method of expressing at least one transgene in a plant comprises growing a plant comprising a gene expression cassette comprising a *Zea mays* metallothionein-like 3'-UTR operably linked to at least one transgene. In an embodiment, a method of expressing at least one transgene in a plant comprises growing a plant comprising a gene expression cassette comprising a *Zea mays* metallothionein-like promoter, and a *Zea mays* metallothionein-like 3'-UTR, and a *Zea mays* metallothionein-like 5'-UTR operably linked to at least one transgene. In an embodiment, a method of expressing at least one transgene in a plant comprises growing a plant comprising a gene expression cassette comprising a 3'-UTR operably linked to at least one transgene.

In an embodiment, a method of expressing at least one transgene in a plant tissue or plant cell comprises culturing a plant tissue or plant cell comprising a gene expression cassette a *Zea mays* metallothionein-like promoter operably linked to at least one transgene. In an embodiment, a method of expressing at least one transgene in a plant tissue or plant cell comprises culturing a plant tissue or plant cell comprising a gene expression cassette a *Zea mays* metallothionein-like 3'-UTR operably linked to at least one transgene. In an embodiment, a method of expressing at least one transgene in a plant tissue or plant cell comprises culturing a plant tissue or plant cell comprising a gene expression cassette a *Zea mays* metallothionein-like promoter and a *Zea mays* metallothionein-like 3'-UTR, and a *Zea mays* metallothionein-like 5'-UTR operably linked to at least one transgene. In an embodiment, a method of expressing at least one transgene in a plant tissue or plant cell comprises culturing a plant tissue or plant cell comprising a gene expression cassette comprising a 3'-UTR operably linked to at least one transgene.

In an embodiment, a plant, plant tissue, or plant cell comprises a *Zea mays* metallothionein-like maize gene promoter. In an embodiment, a *Zea mays* metallothionein-like promoter can be SEQ ID NO:1 or SEQ ID NO:2. In an embodiment, a plant, plant tissue, or plant cell comprises a gene expression cassette comprising a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1 or SEQ ID NO:2. In an embodiment, a plant, plant tissue, or plant cell comprises a gene expression cassette comprising a *Zea mays* metallothionein-like promoter that is operably linked to a transgene. In an illustrative embodiment, a plant, plant tissue, or plant cell comprises a gene expression cassette comprising a *Zea mays* metallothionein-like promoter that is operably linked to a transgene, wherein the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof.

In an embodiment, a plant, plant tissue, or plant cell comprises a *Zea mays* metallothionein-like 5'-UTR. In an embodiment, a *Zea mays* metallothionein-like 5'-UTR can be a polynucleotide of SEQ ID NO:5. In an embodiment, a plant, plant tissue, or plant cell comprises a gene expression cassette comprising a 5'-UTR, wherein the 5'-UTR is at least 80%, 85%, 90%, 91%, 92%, 93%, 94%, 95%, 96%, 97%, 98%, 99%, 99.5%, 99.8%, or 100% identical to SEQ ID NO:5. In an embodiment, a gene expression cassette comprises a *Zea mays* metallothionein-like 5'-UTR that is operably linked to a promoter, wherein the promoter is a *Zea mays* metallothionein-like promoter, or a promoter that originates from a plant (e.g., *Zea mays* ubiquitin 1 promoter), a virus (e.g., Cassava vein mosaic virus promoter) or a bacteria (e.g., *Agrobacterium tumefaciens* delta mas). In an embodiment, a plant, plant tissue, or plant cell comprises a gene expression cassette comprising a *Zea mays* metallothionein-like 5'-UTR that is operably linked to a transgene. In an illustrative embodiment, a plant, plant tissue, or plant cell comprising a gene expression cassette comprising a *Zea mays* metallothionein-like 5'-UTR that is operably linked to a transgene, wherein the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof.

Transgenic Plants

In an embodiment, a plant, plant tissue, or plant cell comprises a gene expression cassette comprising a 3'-UTR. In an embodiment, a plant, plant tissue, or plant cell comprises a gene expression cassette comprising a *Zea mays* metallothionein-like 3'-UTR. In an embodiment, the *Zea mays* metallothionein-like 3'-UTR is a polynucleotide of SEQ ID NO:3 or SEQ ID NO:4. In an embodiment, a plant, plant tissue, or plant cell comprises a gene expression cassette comprising a 3'-UTR, wherein the 3'-UTR is at least 80%, 85%, 90%, 91%, 92%, 93%, 94%, 95%, 96%, 97%, 98%, 99%, 99.5%, 99.8%, or 100% identical to SEQ ID NO:3 or SEQ ID NO:4.

In an embodiment, a gene expression cassette comprises a *Zea mays* metallothionein-like 3'-UTR that is operably linked to a promoter, wherein the promoter is a *Zea mays* metallothionein-like promoter, or a promoter that originates from a plant (e.g., *Zea mays* ubiquitin 1 promoter), a virus (e.g., Cassava vein mosaic virus promoter) or a bacteria (e.g., *Agrobacterium tumefaciens* delta mas). In an embodiment, a plant, plant tissue, or plant cell comprises a gene expression cassette comprising a *Zea mays* metallothionein-like 3'-UTR that is operably linked to a transgene. In an illustrative embodiment, a plant, plant tissue, or plant cell comprising a gene expression cassette comprising a *Zea mays* metallothionein-like 3'-UTR that is operably linked to a transgene, wherein the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof.

In an embodiment, a plant, plant tissue, or plant cell comprises a gene expression cassette comprising a *Zea mays* metallothionein-like promoter, *Zea mays* metallothionein-like 5'-UTR, and a *Zea mays* metallothionein-like 3'-UTR that are operably linked to a transgene. The promoter, 5'-UTR, and 3'-UTR can be operably linked to different transgenes within a gene expression cassette when a gene expression cassette includes two or more transgenes. In an illustrative embodiment, a gene expression cassette comprises a *Zea mays* metallothionein-like promoter that is operably linked to a transgene, wherein the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof. In an illustrative embodiment, a gene expression cassette comprises a *Zea mays* metallothionein-like 5'-UTR that is operably linked to a transgene, wherein the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof. In an embodiment, a gene expression cassette comprises a *Zea mays* metallothionein-like 5'-UTR that is operably linked to a promoter, wherein the promoter is a *Zea mays* metallothionein-like promoter, or a promoter that originates from a plant (e.g., *Zea mays* ubiquitin 1 promoter), a virus (e.g., Cassava vein mosaic virus promoter) or a bacterium (e.g., *Agrobacterium tumefaciens* delta mas). In an illustrative embodiment, a gene expression cassette comprises a *Zea mays* metallothionein-like 3'-UTR that is operably linked to a transgene, wherein the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof.

In an embodiment, transgene expression using methods described herein is specific to a plant's roots. In an embodiment, transgene expression includes more than one transgene expressed in the roots. In an embodiment, a method of growing a transgenic plant as described herein includes root-specific transgene expression. In an embodiment, a method of expressing a transgene in a plant tissue or plant cell includes root-specific tissues and root-specific cells. In an embodiment, the root-specific expression includes maize root-specific expression.

In an embodiment, a plant, plant tissue, or plant cell comprises a vector comprising a *Zea mays* metallothionein-like promoter, *Zea mays* metallothionein-like 5'-UTR, and/ or *Zea mays* metallothionein-like 3'-UTR as disclosed herein. In an embodiment, a plant, plant tissue, or plant cell comprises a vector comprising a *Zea mays* metallothionein-like promoter, *Zea mays* metallothionein-like 5'-UTR, and/ or *Zea mays* metallothionein-like 3'-UTR as disclosed herein operably linked to a transgene. In an embodiment, a plant, plant tissue, or plant cell comprises a vector comprising a gene expression cassette as disclosed herein. In an embodiment, a vector can be a plasmid, a cosmid, a bacterial artificial chromosome (BAC), a bacteriophage, or a virus.

In accordance with one embodiment a plant, plant tissue, or plant cell is provided wherein the plant, plant tissue, or plant cell comprises a non-endogenous promoter sequence operably linked to a transgene, wherein the promoter sequence comprises a sequence SEQ ID NO:1 or SEQ ID NO:2 or a sequence having 90. 95, 98 or 99% sequence identity with SEQ ID NO:1 or SEQ ID NO:2. In one embodiment a plant, plant tissue, or plant cell is provided wherein the plant, plant tissue, or plant cell comprises SEQ ID NO:1, or a sequence that has 90% sequence identity with SEQ ID NO:1 operably linked to a transgene. In one embodiment a plant, plant tissue, or plant cell is provided wherein the plant, plant tissue, or plant cell comprises SEQ ID NO:2, or a sequence that has 90% sequence identity with SEQ ID NO:2 operably linked to a transgene. In one embodiment the plant, plant tissue, or plant cell is a dicotyledonous or monocotyledonous plant or a cell or tissue derived from a dicotyledonous or monocotyledonous plant. In one embodiment the plant is selected from the group consisting of maize, wheat, rice, sorghum, oats, rye, bananas, sugar cane, soybean, cotton, sunflower, and canola. In one embodiment the plant is *Zea mays*. In accordance with one embodiment the plant, plant tissue, or plant cell comprises SEQ ID NO:1 or SEQ ID NO:2 or a sequence having 90. 95, 98 or 99% sequence identity with SEQ ID NO:1 or SEQ ID NO:2 operably linked to a transgene. In one embodiment the plant, plant tissue, or plant cell comprises a promoter operably linked to a transgene wherein the promoter consists of SEQ ID NO:1 or SEQ ID NO:2 or a sequence having 90. 95, 98 or 99% sequence identity with SEQ ID NO:1 or SEQ ID NO:2. In accordance with one embodiment the gene construct comprising non-endogenous promoter sequence operably linked to a transgene is incorporated into the genome of the plant, plant tissue, or plant cell.

In one embodiment a non-*Zea* plant (i.e., not a member of the *Zea* family), plant tissue, or plant cell is provided comprising SEQ ID NO:1 or SEQ ID NO:2, or a sequence that has 90, 95, 98 or 99% sequence identity with SEQ ID NO:1 or SEQ ID NO:2, operably linked to a transgene. In accordance with one embodiment the non-*Zea* plant, plant tissue, or plant cell is a dicotyledonous or monocotyledonous plant or plant cell or tissue derived from a dicotyledonous or monocotyledonous plant. In one embodiment the plant is selected from the group consisting of, wheat, rice, sorghum, oats, rye, bananas, sugar cane, soybean, cotton, sunflower, and canola. In accordance with one embodiment the promoter sequence operably linked to a transgene is incorporated into the genome of the plant, plant tissue, or plant cell. In one embodiment the plant, plant tissue, or plant cell further comprises a 5' untranslated sequence comprising SEQ ID NO:5 or a sequence that has 90% sequence identity with SEQ ID NO:5, wherein the 5' untranslated sequence is inserted between, and operably linked to, said promoter and said transgene.

In one embodiment a non-*Zea* plant, plant tissue, or plant cell is provided that comprises SEQ ID NO:1 or SEQ ID NO:2, or a sequence that has 90, 95, 98 or 99% sequence identity with SEQ ID NO:1 or SEQ ID NO:2, operably linked to the 5' end of a transgene and a 3' untranslated sequence comprising SEQ ID NO:3 or SEQ ID NO:4 or a sequence that has 90% sequence identity with SEQ ID NO:3 or SEQ ID NO:4, wherein the 3' untranslated sequence is operably linked to said transgene. In accordance with one embodiment the non-*Zea* plant, plant tissue, or plant cell is a dicotyledonous or monocotyledonous plant or is a plant issue or cell derived from a dicotyledonous or monocotyledonous plant. In one embodiment the plant is selected from the group consisting of wheat, rice, sorghum, oats, rye, bananas, sugar cane, soybean, cotton, sunflower, and canola. In accordance with one embodiment the promoter sequence operably linked to a transgene is incorporated into the genome of the plant, plant tissue, or plant cell. In one embodiment the plant, plant tissue, or plant cell further comprises a 5' untranslated sequence comprising SEQ ID NO:5 or a sequence that has 90% sequence identity with SEQ ID NO:5, wherein the 5' untranslated sequence is inserted between, and operably linked to, said promoter and said transgene. In one embodiment the 5' untranslated sequence consists of SEQ ID NO:5.

In one embodiment a non-*Zea* plant, plant tissue, or plant cell is provided that comprises SEQ ID NO:39, or a sequence having 90% sequence identity with SEQ ID NO:1 or SEQ ID NO:2 operably linked to a transgene. In one embodiment a non-*Zea* plant, plant tissue, or plant cell is provided that comprises a promoter operably linked to a transgene, wherein the promoter consists of SEQ ID NO:1 or SEQ ID NO:2, or a sequence having 90% sequence identity with SEQ ID NO:1 or SEQ ID NO:2. In one embodiment the 3' untranslated sequence comprises or consists of SEQ ID NO:3 or SEQ ID NO:4 or a sequence that has 90% sequence identity with SEQ ID NO:3 or SEQ ID NO:4, wherein the 3' untranslated sequence is operably linked to 3' end of the transgene.

In an embodiment, a plant, plant tissue, or plant cell according to the methods disclosed herein can be a monocotyledonous plant. The monocotyledonous plant, plant tissue, or plant cell can be, but not limited to corn, rice, wheat, sugarcane, barley, rye, sorghum, orchids, bamboo, banana, cattails, lilies, oat, onion, millet, and triticale.

In an embodiment, a plant, plant tissue, or plant cell according to the methods disclosed herein can be a dicotyledonous plant. The dicotyledonous plant, plant tissue, or plant cell can be, but not limited to rapeseed, canola, Indian mustard, Ethiopian mustard, soybean, sunflower, and cotton.

With regard to the production of genetically modified plants, methods for the genetic engineering of plants are well known in the art. For instance, numerous methods for plant transformation have been developed, including biological and physical transformation protocols for dicotyledonous plants as well as monocotyledonous plants (e.g., Goto-Fumiyuki et al., *Nature Biotech* 17:282-286 (1999); Miki et al., Methods in Plant Molecular Biology and Biotechnology, Glick, B. R. and Thompson, J. E. Eds., CRC Press, Inc., Boca Raton, pp. 67-88 (1993)). In addition, vectors and in vitro culture methods for plant cell or tissue transformation and regeneration of plants are available, for example, in Gruber et al., Methods in Plant Molecular Biology and Biotechnology, Glick, B. R. and Thompson, J. E. Eds., CRC Press, Inc., Boca Raton, pp. 89-119 (1993).

One of skill in the art will recognize that after the exogenous sequence is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed cells can also be identified by screening for the activities of any visible marker genes (e.g., the yfp, gfp, β-glucuronidase, luciferase, B or C1 genes) that may be present on the recombinant nucleic acid constructs. Such selection and screening methodologies are well known to those skilled in the art.

Physical and biochemical methods also may be used to identify plant or plant cell transformants containing inserted gene constructs. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) next generation sequencing (NGS) analysis; 5) protein gel electrophoresis, western blot techniques, immunoprecipitation, or enzyme-linked immunosorbent assay (ELISA), where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, Northern blots of the RNA (e.g., mRNA) isolated from the tissues of interest. Typically, if the mRNA is present or the amount of mRNA has increased, it can be assumed that the corresponding transgene is being expressed. Other methods of measuring gene and/or encoded polypeptide activity can be used. Different types of enzymatic assays can be used, depending on the substrate used and the method of detecting the increase or decrease of a reaction product or by-product. In addition, the levels of polypeptide expressed can be measured immunochemically, i.e., ELISA, RIA, EIA and other antibody based assays well known to those of skill in the art, such as by electrophoretic detection assays (either with staining or western blotting). As one non-limiting example, the detection of the AAD-1 (aryloxyalkanoate dioxygenase; see WO 2005/107437) and PAT (phosphinothricin-N-acetyltransferase) proteins using an ELISA assay is described in U.S. Patent Publication No. 2009/0093366, herein incorporated by reference in its entirety. The transgene may be selectively expressed in some cell types or tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed comprises the transgene or gene expression cassette. The present disclosure further encompasses the progeny, clones, cell lines or cells of the transgenic plants described above wherein said progeny, clone, cell line or cell comprise the transgene or gene construct.

While the invention has been described with reference to specific methods and embodiments, it will be appreciated that various modifications and changes may be made without departing from the invention.

EXAMPLES

Example 1

Identification of High Expressing Regulatory Elements

Novel *Zea mays* metallothionein-like regulatory elements were identified via two approaches: 1) a bioinformatics approach by profiling the public gene expression data and, 2) a transcriptional profiling approach by using next generation sequencing (NGS). These regulatory elements were then identified, isolated, and cloned to characterize the expression profile of the regulatory elements for use in of transgenic plants. Transgenic maize lines stably transformed with a cry34Ab1 gene isolated from *Bacillus thuringiensis* and an aad-1 selectable marker gene were produced and the transgene expression levels and tissue specificity was assessed. As such novel *Zea mays* metallothionein-like regulatory elements were identified and characterized. Disclosed for the first time are promoter, 5'-UTR and 3'-UTR regulatory elements for use in gene expression constructs.

Bioinformatics Approach

Three sources of data were utilized to identify high expressing maize genes in root and shoot tissues of maize seedlings: 1) 35,000 maize gene sequences and their annotations present in the maize database (available at www.maizegdb.org) in 2010; 2) gene expression data for total maize transcriptome for V4 shoots and roots (Wang, et al., (2009): Genome-Wide and Organ-Specific Landscapes of Epigenetic Modifications and Their Relationships to mRNA and Small RNA Transcriptomes in Maize. *Plant Cell* 21:1053-1069); and 3) full-length cDNA sequences of 9,000 genes (Alexandrov N., et al., (2009): Insights into corn genes derived from large-scale cDNA sequencing. *Plant Molecular Biology* 69:179-194). The gene expression data were aligned for the 9,000 full-length cDNA sequences and 35,000 maize genes. Based on fragments per kilobase of exon per million fragments mapped (FPKM) values, a quantitative measure of gene expression, 100 high expressing genes were identified from each of the maize root and shoot gene expression data sets (FIG. 1). Next, these sequences were mapped to the 35,000 maize genes, which aligned to 500 expressing genes or about 1.4% of the highest expressing genes of the maize genome. From this data set, 100 expressing genes were identified for leaf and for root tissue expression. To further reduce the number of genes, quantitative PCR was performed on cDNA samples isolated from three leaf and root development stages each using gene-specific primers.

Transcriptional Profiling Approach

Maize tissues were obtained from plants grown to different stages of plant growth and development for transcriptional profiling in order to identify and select regulatory elements of native maize genes with desired expression profiles for use in gene expression cassettes. For example, tissue samples from 3 stages of leaf (V4 (duplicate), V12 and R3) and root (V4 and V12 nodal and fibrous tissues) development, pollen, silk, cob, immature kernel (20 day after pollination), husk and stem (V4 and R1) were collected. Total mRNA was isolated from all of the above described tissues and high quality mRNA in desired quantities were obtained.

Next, cDNA libraries were prepared from each of the mRNA samples and high-throughput sequencing was completed using a Illumina HiSeq® 2000 (Illumina Inc., San Diego, Calif.). In addition, the Illumina TruSeq® RNA sample preparation kit was used according to the manufacturer's recommended protocol for RNAseq sample preparation. In brief, 5 µg of total RNA was purified using poly-T oligo-attached magnetic beads followed by fragmentation into smaller pieces (about 200 bp average length) using divalent cations under high temperature. Next, SuperScript® II reverse transcriptase and random primers were then used to copy the fragmented mRNA into first strand cDNA. The cDNA was further converted into double stranded cDNA (ds cDNA) using DNA polymerase I and RNase H. The double stranded cDNA fragments then went through end repair, A-tailing, and then ligation to indexed Illumina paired-end (PE) adapters. Finally, library products were cleaned up and enriched with 15 cycles of PCR and purified. The enriched libraries were normalized to a concentration of 2 nM, denatured with sodium hydroxide, and diluted to 12 pM in hybridization buffer for loading onto a single lane of a HiSeq® flow cell. Cluster generation, primer hybridization and sequencing reactions were carried out according to an Illumina manufacturer recommended sequencing protocol.

Figure 2:
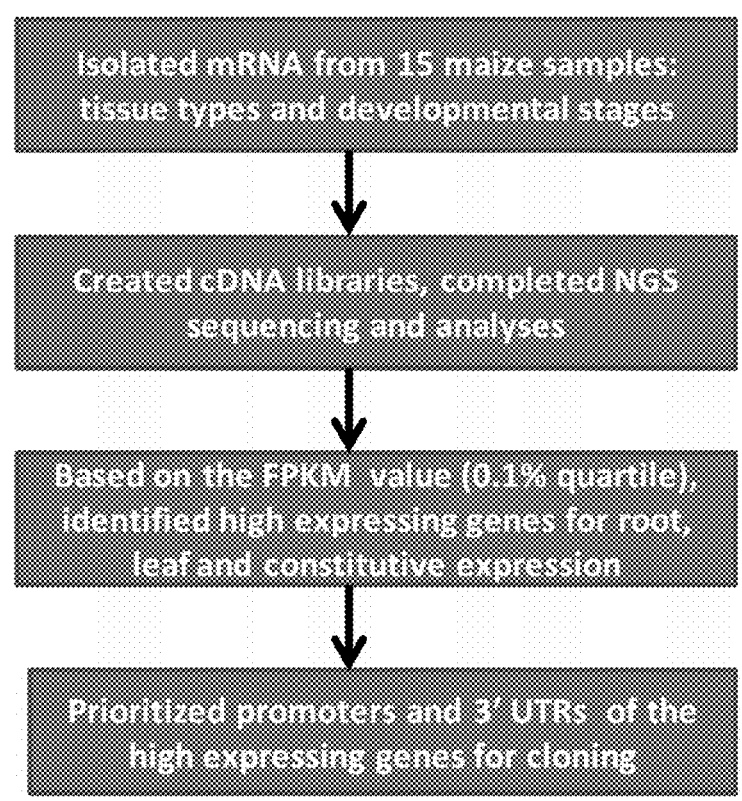
FIG. 2 is a schematic flow chart displaying the process of identifying high expressing genes in maize using a transcriptional profiling approach with Next Generation Sequencing (NGS).

The sequencing reads were then filtered to remove low quality reads. About 99.9% of the sequencing reads were retained after filtering. The sequencing reads were aligned to the annotated *Zea mays* c.v. B73 genome available in the maizeGDB. Sequencing reads that mapped onto the maize genome at more than one locus were discarded to avoid confusion in identification of the high expressing genes and their further characterization. This step led to alignment of >70% sequencing reads from each of the samples to the maize genome. The quantitative gene expression unit of fragments per kilobase of exon per million fragments mapped or FPKM values were used to rank genes for stable transformation testing that matched a desirable expression pattern for use in gene expression constructs. Approximately 15-20 high expressing genes, which represented ~0.1% of the most highly expressed genes in maize were prioritized for testing in stable transgenic lines (FIG. 2).

Example 2

Vector Construction

The promoter, 5'-UTR, and 3'-UTR sequences were extracted from the *Zea mays* metallothionein-like gene sequence that was identified from the bioinformatics and transcriptional profiling approaches previously described. The native sequence of the *Zea mays* metallothionein-like gene, from the *Zea may c.v. B*73 genome is provided as SEQ ID NO:6. The 2,061 bp promoter sequence (SEQ ID NO:1) is italicized; the ATG and TGA translational start and stop codons flanking the coding sequence are shown in bold font. The 81 bp 5'-UTR sequence (SEQ ID NO:5) is shown in capital letters. The 1,080 bp 3'-UTR sequence (SEQ ID NO:3) is underlined.

Figure 3:
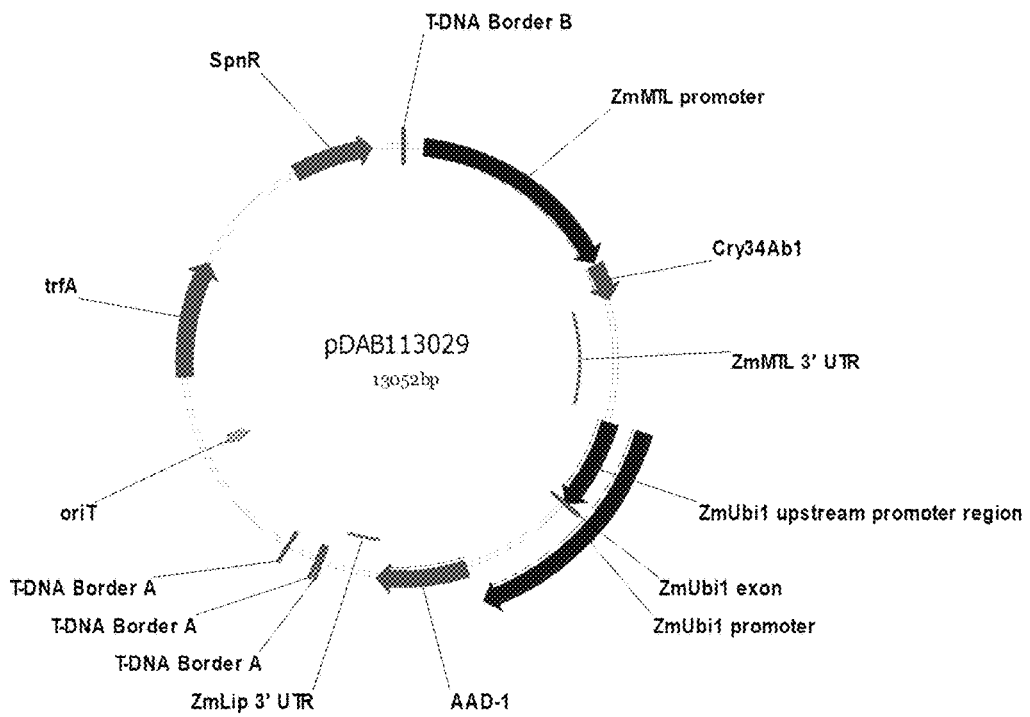
FIG. 3 shows the pDAB113029 vector plasmid map depicting a gene expression cassette comprising the full length *Zea mays* metallothionein-like promoter and 3'-UTR regulatory elements controlling the expression of a cry34Ab1 reporter gene.

(SEQ ID NO: 6)
accatatcatgtctcaagccttaatacactttaaat aaatttaaatcatttaatagaaactaattacatgttaatacatcactata aaaaaaattaatggttgcaccgtaaagctttaacttgtgcatctatactc taatagtttgtggtccaacgcctcggtccgacatctatagaagtcttttt ttctttattatttggtttctttgtgagcttcacgttcagtttggccctat ttgtactcttgcatatacttatagatatgtaacatgttttctaacatctt gcttgagatgttattcattcgaagcatccctttgtctaagtccacttgtg cacccctttgaaaaaatgttagcataaatgattgtgttaaccatcaaaaca ccaaaactttattttaaacggacctaagtctattttacttgcaatgagct agcatgaggaacatggagcaacattaaactcgaaacaggaggcagtatca aatactccctctgtttcttttattagtcgctggatagtgaaattttgca ctatccagcgactaataaaaagaaacggagggagtatgagagtcgatctt aagaacatgacgtatgatccatacccctcaaatctgtttgagaaaaatcac tatcgaaggaggctacttgttttcttctttgcgtagaagataatactcct cctgtcctaaattaatatttgtttaaacttttttactaaattcatgtaata attaatgtatgcgttatatatatatgtctaggtttataattattcatatg aatatgaacataaaaatctagggctaaaacgactactattttgaaaacgg aaggagtagtaagttattttaagcggaggggaaccatgatgggctagtgat ttaatttacatatatatattggtgttctgggctcttacatgagaagatct agttaactgttgttactgaacagcgaagacaaatatataatttaagctcc ccaactgctagtgattctgttaagaggtaatgtttaaagtaaatttacaa gagcccgtctagctcagtcggtagagcgcaaggctcttaaccttgtggtc gtgggttcgagcccacggtgggcgcacaattttttgttttttgacattt tttgtttgcttagttgcagacggttttccctgctaggagatttccgag agaaaaaaaggcactacaggttaaccaaaaccaccaaccctttggagcgt cgaggcgacgggcatttgcgtagttgaagcttacaaagttgcatatgaga tgagtgccgacatgaagcggataacgttttaaactggcaacaatatcta gctgtttcaaattcaggcgtgggaagctacgcctacgcgccctggacggc gtgtaaagagccagcatcggcatcattgtcaaacgatcgacaaggccaag aaattccaaatatattaataaaaaagaaggcacaaattagtttggtt ttttagtatgtgtgcggaggaaatttgagaacgaacgtatcaagaag gcacaagacgatatagattgacgcggctagaagttgcagcaagacagtgg gtacggtatatatcctaataaataaaaaataaaactatagtgtgtcaa atgtcaacaagaggaggaggcagccaaattagcagagggagacaagtaga gcacgccttattagcttgcttatttatcgtggtggtgtacttgttaatta ctggcacgcattatcaacaacgcagttctggatgtgaatctagacaaaca tttgtctaggttccgcacgtatagttttttttctttttttttgggggg gggtggggggggggggaacggaagctgtaataaacggtactaggaacga aagcaaccgccgcgcgcatgttttgcaatagattacggtgaccttgatg caccaccgcgtgctataaaaaccagtgtccccgagtctactcatcaacca -continued atccataactcgaaacctttcttgtgctctgttctgtctgtgtgtttcc aaagcaaacgaaagaggtcgaggATGtcttgcagctgcggatcaagctgc aactgcggatcaagctgcaagtgcgggtaatgtaattaaggctcttatta cctttctgtaactgtgtgatcgtgtcctttgtgaattgtacgtggtgtc ttttttttttaatttttttttttttgcttaattctgcgcagcaagatgtac cctgacctggaggagaagagcggcggggcgctcaggccagcgccgccgc cgtcgtcctcggcgttgccctgagacgaagaaggcggcgcagttcgagg cggcgggcgagtccggcgaggccgctcacggctgcagctgcggtgacagc tgcaagtgcagcccctgcaactgcTGAtcctgctgcgttgtttcgtttgc ggcatgcatggatgtcacctttttttttactgtctgctttgtgcttgtggc gtgtcaagaataaaggatggagccatcgtctggtctgactctggctctcc gccatgcatgcttggtgtcggttctgttgtgcttgtgttggtgcatgtaa tcgtatggcatcgttacacaccatgcatctctgatctctttgcgccagtg tgtgtgactatgtccctgtaacgattggctcagtgattgaatatatatac aatactgttttactaagtaagtatgattacctcttatttaaatttctct atgtaaatcatgtcttctacacagtatgttgtacgaccactatctgctga atgtatagatgtctagaaagcacgtggcccgttagcatgacacgaagcac ggttttttagcacgacacaaattaacatgggcccaggctcagcccggccc agcgagcgtgtcggctcgacagccatcccgacgcgttgggctggcccga gcacggcccggtggatgttgggcttagaaaccggcccgctacattttagc gcagcctaaccactgcccaccaatactccgcaattccgcataaatcccc cagtgccccatcccagcccattgaccagcgcgacagctagggctggaaa aaaagctcgaggctcgcgagccagctcgggctcgatcaggctcggctcgg ctcggtgaggctcgcgagcctaaacgagcccgagccgagcctaattccgc agctcgctacactaacgagccgagccggcttggtgaggctcgcgagcggg ctcaaggcttggtccaaactactacttactcgtatctccgttcaccagtg tgtaagtgtgctgattggtcacaactcacaaggaactagagtgcagggac ataatttttattatatggaacatattgtgcttcaaatttgagctaatga ctataattattgttgttgagtacttgagtgtacaggctcgcgagcctata tcgagccgagcctcattaccgagctcgctaagtgaccgagccgagcctgg ctcggc The DNA elements were synthesized and cloned into entry vectors. The promoter and 3'-UTR lengths were 2,061 bp and 1,080 bp, respectively. The *Zea mays* metallothionein-like promoter, cry34Ab1 (reporter gene from *B. thurengiensis*), and the *Zea mays* metallothionein-like 3'-UTR were amplified with primers containing a minimum 15 bp overlapping homology to their flanking DNA element. All fragments were gel purified. All three fragments along with an entry vector backbone, pENTR11, were assembled in a directional order through a Geneart® Seamless cloning reaction (Invitrogen, Carlsbad, Calif.). A Gateway® LR Clonase® (Invitrogen) reaction was then performed with the resulting entry plasmid, pDAB113010, and a destination vector, pDAB104153, leading to a final expression vector, pDAB113029. The destination vector contained a selectable marker cassette comprised of an aad-1 gene driven by the Zea mays ubiquitin-1 promoter (Christensen et al., (1992) *Plant Molecular Biology* 18; 675-689) and terminated by a maize lipase 3'-UTR (U.S. Pat. No. 7,179,902). The resulting construct, pDAB113029 is a heterologous expression construct that contains an aad-1 gene expression cassette and a cry34Ab1 gene expression construct (FIG. 3).

Figure 4:
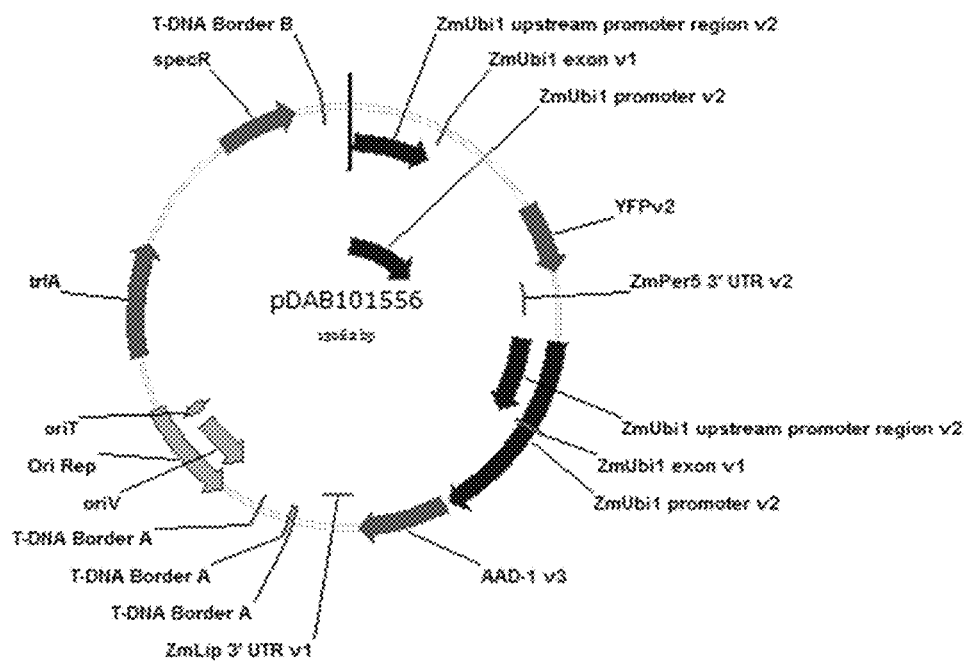
FIG. 4 shows a map of pDAB101556 control vector containing an yfp reporter gene in place of the cry34Ab1 reporter gene present in the test promoter construct, pDAB113029. The yfp gene expression was driven by the *Zea mays* ubiquitin-1 (ZmUbi1) promoter and terminated by the *Zea mays* Per5 (ZmPer5) 3'-UTR.
Figure 5:
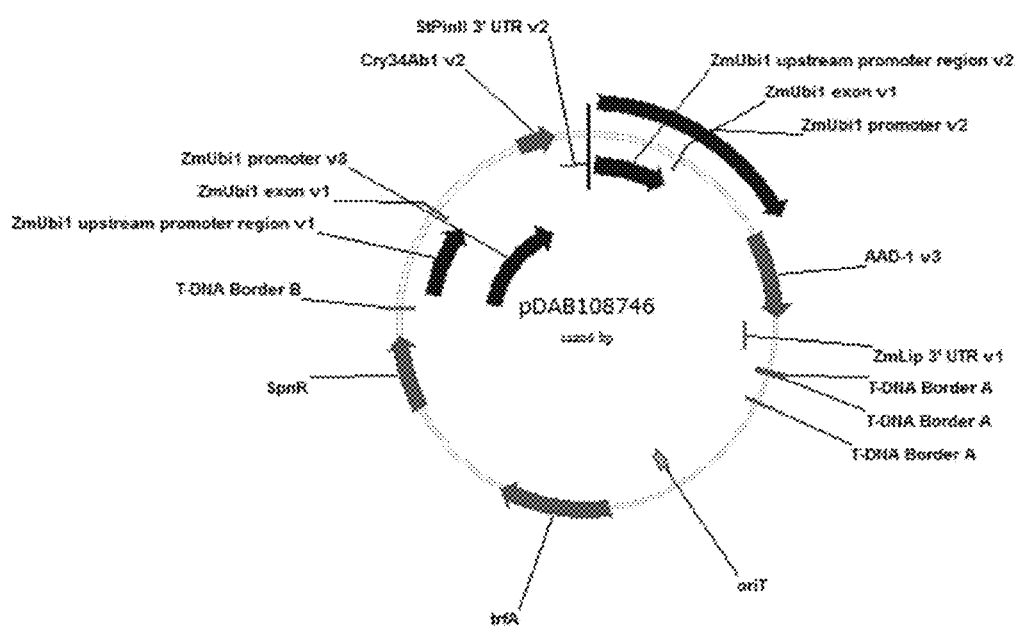
FIG. 5 shows a map of pDAB108746, a positive control vector containing the cry34Ab1 reporter gene driven by the ZmUbi1 promoter and terminated by the StPinII 3'-UTR.

A negative control construct, pDAB101556, was assembled containing a yellow fluorescence protein (YFP; Shagin et al., (2004) *Mol Biol Evol* 21; 841-50) reporter gene instead of the cry34Ab1 gene (FIG. 4) and the same aad-1 expression cassette as present in pDAB113029. A positive control construct, pDAB108746, was built comprised of the *Zea mays* ubiquitin-1 promoter and *Solanum tuberosum* protease inhibitor gene II 3' UTR (StPinII 3'-UTR v2; An et al., (1989) *Plant Cell* 1; 115-22) controlling the expression of the cry34Ab1 gene (FIG. 5). The aad-1 cassette was the same as present in pDAB113029.

Example 3

Figure 7:
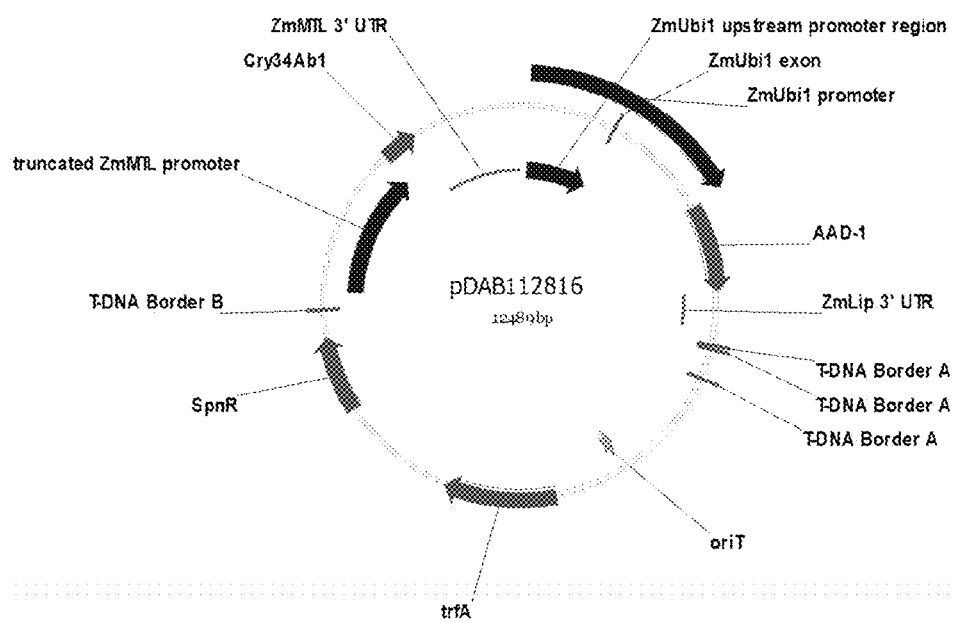
FIG. 7 shows the vector plasmid map of pDAB112816, depicting a gene expression cassette comprising the truncated *Zea mays* metallothionein-like promoter, cry34Ab1 reporter gene and full-length *Zea mays* metallothionein-like 3'-UTR.

Truncation of the *Zea mays* Metallothionein-Like Promoter to Remove Repeated DNA Sequences The 2,061 bp *Zea mays* metallothionein-like promoter sequence of pDAB113029 (SEQ ID NO:1) was truncated to a 1,498 bp *Zea mays* metallothionein-like promoter sequence (SEQ ID NO:2) by removing type/class II transposons, class I transposable elements, class II transposable elements and class III transposable elements as described in the maize transposable element database available at www.maizegdb.org (e.g., RLX_ruda_AC206281_9164 repeats and Zm_CACTA_20 repeats). An alignment comparing the truncated *Zea mays* metallothionein-like promoter and the full length metallothionein-like promoter is provided in FIG. 6. The truncated *Zea mays* metallothionein-like promoter was cloned upstream of the cry34Ab1 reporter and the full-length *Zea mays* metallothionein-like 3'-UTR. The resulting gene expression cassette was assembled into an entry vector pENTR11 with a Geneart® Seamless cloning reaction (Invitrogen). The resulting entry plasmid, pDAB112814, and a destination vector, pDAB104153, were combined into a final expression vector, pDAB112816, with a Gateway® LR Clonase® (Invitrogen) reaction. The destination vector pDAB112816 contained a selectable marker cassette comprising an aad-1 gene driven by the *Zea mays* ubiquitin-1 promoter and terminated by a maize lipase 3'-UTR (FIG. 7).

Example 4

Figure 9:
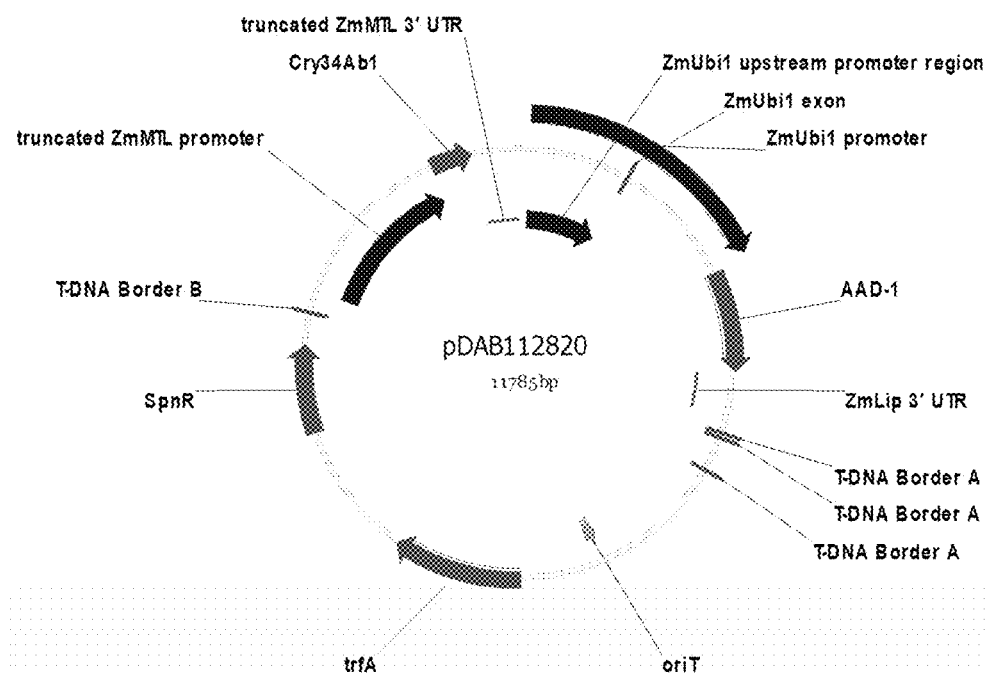
FIG. 9 shows the plasmid vector map of pDAB112820, depicting a gene expression cassette comprised of the truncated *Zea mays* metallothionein-like promoter, cry34Ab1 reporter gene and truncated *Zea mays* metallothionein-like 3'-UTR.

Truncation of the *Zea mays* Metallothionein-Like 3'-UTR to Remove Repeated DNA Sequences The 1,080 bp *Zea mays* metallothionein-like 3'-UTR sequence (SEQ ID NO:3) of pDAB113029 was truncated to a 376 bp *Zea mays* metallothionein-like 3'-UTR sequence (SEQ ID NO:4) by removing repeats of class I retroelements and type/class II transposons as described in the maize transposable element database available at www.maizegdb.org. An alignment comparing the truncated *Zea mays* metallothionein-like 3'-UTR and the full length *Zea mays* metallothionein-like 3'-UTR is provided in FIG. 8. The resulting truncated *Zea mays* metallothionein-like 3'-UTR was then assembled with the *Zea mays* metallothionein-like truncated promoter (SEQ ID NO:2) the cry34Ab1 reporter gene into an entry backbone, pENTR11 with the Geneart® Seamless cloning reaction (Invitrogen). The resulting construct, pDAB112817, and a destination vector, pDAB104153, were combined into a final expression vector, pDAB112820, with a Gateway® LR Clonase® (Invitrogen) reaction. The destination vector pDAB112820 contained a selectable marker cassette comprising an aad-1 gene controlled by the *Zea mays* ubiquitin-1 promoter and terminated by maize lipase 3'-UTR (FIG. 9).

Example 5

Plant Transformation and Molecular Confirmation

Experimental constructs were transformed into maize via *Agrobacterium*-mediated transformation of immature embryos isolated from the inbred line, *Zea mays* c.v. B104. The method used is similar to those published by Ishida et al., (1996) and Frame et al., (2006) but with several modifications and improvements to make the method amenable to high throughput transformation in an industrial setting. Ishida Y. et al., (1996) High efficiency transformation of maize (*Zea mays* L.) mediated by *Agrobacterium tumefaciens*. *Nature Biotechnol* 14:745-750; and Frame et al., (2006) Improved *Agrobacterium*-mediated transformation of three maize inbred lines using MS salts. *Plant Cell Rep* 25: 1024-1034.

Transformation of *Agrobacterium tumefaciens*

The binary expression vectors were transformed into *Agrobacterium tumefaciens* strain DAt13192 (RecA deficient ternary strain) (Int'l. Pat. Pub. No. WO2012016222). Bacterial colonies were selected, and binary plasmid DNA was isolated and confirmed via restriction enzyme digestion.

*Agrobacterium* Culture Initiation

*Agrobacterium* cultures were streaked from glycerol stocks onto AB minimal medium (Gelvin, S., 2006, *Agrobacterium* Virulence Gene Induction, in Wang, K., ed., *Agrobacterium Protocols Second Edition* Vol. 1, Humana Press, p. 79; made without sucrose and with 5 g/L glucose and 15 g/L Bacto™ Agar) and incubated at 20° C. in the dark for 3 days. *Agrobacterium* cultures were then streaked onto a plate of YEP medium (Gelvin, S., 2006, *Agrobacterium* Virulence Gene Induction, in Wang, K., ed., *Agrobacterium Protocols Second Edition* Vol. 1, Humana Press, p. 79) and incubated at 20° C. in the dark for 1 day.

On the day of an experiment, a mixture of Inoculation medium (2.2 g/L MS salts, 68.4 g/L sucrose, 36 g/L glucose, 115 mg/L L-proline, 2 mg/L glycine, 100 mg/L myo-Inositol, 0.05 mg/L nicotinic acid, 0.5 mg/L pyridoxine HCl, 0.5 mg/L thiamine HCl) and acetosyringone was prepared in a volume appropriate to the size of the experiment. A 1 M stock solution of acetosyringone in 100% dimethyl sulfoxide was added to the Inoculation medium to make a final acetosyringone concentration of 200 µM.

For each construct, 1-2 loops of *Agrobacterium* from the YEP plate were suspended in 15 ml of the inoculation medium/acetosyringone mixture inside a sterile, disposable, 50 ml centrifuge tube and the optical density of the solution at 600 nm ($O.D._{600}$) was measured in a spectrophotometer. The suspension was then diluted down to 0.25-0.35 $O.D._{600}$ using additional Inoculation medium/acetosyringone mixture. The tube of *Agrobacterium* suspension was then placed horizontally on a platform shaker set at about 75 rpm at room temperature for between 1 and 4 hours before use.

Maize Transformation

Experimental constructs were transformed into maize via *Agrobacterium*-mediated transformation of immature embryos isolated from the inbred line, *Zea mays* c.v. B104. The method used is similar to those published by Ishida et al., (1996) Nature Biotechnol 14:745-750 and Frame et al., (2006) Plant Cell Rep 25: 1024-1034, but with several modifications and improvements to make the method amenable to high-throughput transformation. An example of a method used to produce a number of transgenic events in maize is given in U.S. Pat. App. Pub. No. US 2013/0157369 A1, beginning with the embryo infection and co-cultivation steps.

Putative transgenic maize plants were sampled at the V2-3 leaf stage for transgene presence using cry34Ab1 and aad-1 quantitative PCR assays. Total DNA was extracted from the leaf samples, using MagAttract® DNA extraction kit (Qiagen) as per manufacturer's instructions.

To detect the genes of interest, gene-specific DNA fragments were amplified with TaqMan® primer/probe sets containing a FAM-labeled fluorescent probe for the cry34Ab1 gene and a HEX-labeled fluorescent probe for the endogenous invertase reference gene control. The following primers were used for the cry34Ab1 and invertase endogenous reference gene amplifications. The primer sequences were as follows;

```
Cry34Ab1 Primers/probes:
Forward Primer: TQ.8v6.1.F:
                                      (SEQ ID NO: 7)
GCCATACCCTCCAGTTG Reverse Primer: TQ.8v6.1.R:
                                      (SEQ ID NO: 8)
GCCGTTGATGGAGTAGTAGATGG Probe: TQ.8v6.1.MGB.P:
                                      (SEQ ID NO: 9)
5'-/56-FAM/CCGAATCCAACGGCTTCA/MGB Invertase Primers:
Forward Primer: InvertaseF:
                                      (SEQ ID NO: 10)
TGGCGGACGACGACTTGT Reverse Primer: InvertaseR:
                                      (SEQ ID NO: 11)
AAAGTTTGGAGGCTGCCGT InvertaseProbe:
                                      (SEQ ID NO: 12)
5'-/5HEX/CGAGCAGACCGCCGTGTACTT/3BHQ_1/-3'
```

Next, the PCR reactions were carried out in a final volume of 10 µl reaction containing 5 µl of Roche LightCycler® 480 Probes Master Mix (Roche Applied Sciences, Indianapolis, Ind.); 0.4 µl each of TQ.8v6.1.F, TQ.8v6.1.R, Invertase F, and InvertaseR primers from 10 µM stocks to a final concentration of 400 nM; 0.4 µl each of TQ.8v6.1.MGB.P and Invertase Probes from 5 µM stocks to a final concentration of 200 nM, 0.1 µl of 10% polyvinylpyrrolidone (PVP) to final concentration of 0.1%; 2 µl of 10 ng/µl genomic DNA and 0.5 µl water. The DNA was amplified in a Roche LightCycler® 480 System under the following conditions: 1 cycle of 95° C. for 10 min; 40 cycles of the following 3-steps: 95° C. for 10 seconds; 58° C. for 35 seconds and 72° C. for 1 second, and a final cycle of 4° C. for 10 seconds. Cry34Ab1 copy number was determined by comparison of Target (gene of interest)/Reference (Invertase gene) values for unknown samples (output by the LightCycler® 480) to Target/Reference values of cry34Ab1 copy number controls.

The detection of the aad-1 gene was carried out as described above for the cry34Ab1 gene using the invertase endogenous reference gene. The aad-1 primer sequences were as follows;

```
AAD1 Forward Primer:
                                      (SEQ ID NO: 13)
TGTTCGGTTCCCTCTACCAA AAD1 Reverse Primer:
                                      (SEQ ID NO: 14)
CAACATCCATCACCTTGACTGA AAD1 Probe:
                                      (SEQ ID NO: 15)
5'-FAM/CACAGAACCGTCGCTTCAGCAACA-MGB/BHQ-3'
```

Finally, the $T_0$ plants containing the gene of interest were sampled at V4-5 for cry34Ab1 and AAD-1 leaf ELISA assays. Four leaf punches were sampled. Another set of plants were sampled at V4-5 for the entire root mass for both the protein ELISA assays. Leaf and root Cry34Ab1 (Agdia, Inc., Elkart, Ind.) and AAD-1 (Acadia BioScience) ELISA assays were performed as per the manufacturer's instructions. The Cry34Ab1 leaf ELISA assays were expressed as ng/cm$^2$, while the root ELISA results were expressed as parts per million (or ng protein per mg total plant protein). Total root protein assays were carried out with the Bradford detection method as per the manufacturer's instructions.

$T_0$ plants were selfed and crossed to Zea mays c.v. B104 non-transgenic transformation lines to obtain $T_1$ seed. Five-six transgenic lines or events of each of the test regulatory element constructs were advanced for $T_1$ protein and RNA gene expression studies and then to $T_2$ seed production. Accordingly, 30-40 $T_1$ seed of each of the events were sown; seedlings were sprayed with SureII® at the V2-V3 stage of development to kill non-transgenic segregants. The transgenic plants were sampled at multiple stages of plant development for cry34Ab1 and AAD-1 ELISA as follows: leaf (V4, V12 and R3); root (V4 and R1); stem (R1); pollen (R1); silk (R1); husk (R3); kernel (R3); and cob (R3). All tissues were isolated and placed in tubes embedded in dry ice; which were then transferred to −80° C. Frozen tissues were lyophilized prior to protein extraction for ELISA.

Putative transgenic $T_1$ plants containing cry34Ab1, yfp and aad-1 transgenes were sampled at V4-5 for the leaf ELISA assays. Four leaf punches were sampled. The leaf punches were placed into a tube and a single ⅛" stainless steel bead (Hoover Precision Products, Cumming, Ga., USA) was added to each 1.2 ml tube containing 300 µl extraction buffer (1× PBST supplemented with 0.05% Tween 20 and 0.5% BSA). The samples were processed in a Genogrinder™ (SPEX SamplePrep, Metuchen, N.J.) at 1,500 rpm for 4 minutes. The samples were centrifuged at 4,000 rpm for 2 minutes in a Sorvall Legend XFR™ centrifuge. Next, an additional 300 µl of extraction buffer was added and the samples were processed once more in a Genogrinder™ at 1,500 rpm for 2 minutes. The samples were centrifuged once more at 4,000 rpm for 7 minutes. Finally, the supernatant was collected and ELISA assays were completed at different dilutions along with the protein standards using the commercially available Cry34Ab1 (Agdia, Inc.) and AAD-1 (Acadia BioScience, LLC) ELISA assay kits, per the manufacturer's instructions. Protein extraction for various tissue type ELISAs was carried out by grinding the lyophilized tissue in a paint shaker for 30 seconds. For tissues needing further grinding, the grinding step was repeated for another 30 seconds. Garnet powder was added to cover the curved portion at the bottom of the tube. The coarsely ground tissue was transferred to 2 ml tubes and filled up to the 0.5 ml mark. One ceramic ball was added to each tube, as was 0.6 ml of the partial extraction buffer (200 µl of protease inhibitor cocktail, 200 µl of 500 mM EDTA, 15.5 mg DTT powder and PBST to 20 ml). All of the tubes were kept on ice for 10 minutes. The cold tubes were transferred to the 2 ml holder of the Genogrinder®. The samples were ground twice for 30 seconds with a 5 minute cooling on ice in between. Next, 40 µl of 10% Tween®-20 and 300 µl extraction buffer were added to the samples. The samples were ground for another 30 seconds with 5 minutes of cooling in between. Finally, each sample was centrifuged at 13,000 rpm for 7 minutes, and the supernatant was carefully transferred to a new tube to collect the extract. The extract was re-suspended in the extraction buffer and was diluted as needed for ELISA assays.

Example 6

T$_0$ Transgenic Plant Expression Screening

The ELISA results indicated that the *Zea mays* metallothionein-like regulatory elements drove root-specific expression of Cry34Ab1 in T$_0$ events that were transformed with construct, pDAB113029. Negligible expression of Cry34Ab1 by the *Zea mays* metallothionein-like regulatory elements was observed in the leaves and roots (Tables 1 and 2, respectively) of these events. The events produced from the control construct pDAB108746 expressed Cry34Ab1 in both leaf and root tissues. There was no Cry34Ab1 leaf expression observed in plant events transformed with the control construct, pDAB101556, that did not contain the cry34Ab1 gene. All constructs expressed the aad-1 gene in both root and leaf tissues.

TABLE 1

ELISA results showing cry34Ab1 and AAD-1 transgene expression in V4-V6 maize leaves of various construct events.

| Construct Name | No. of Events Analyzed | Mean Cry34 (ng/cm$^2$) | Cry34 STD | Mean AAD-1 (ng/cm$^2$) | AAD-1 STD |
|---|---|---|---|---|---|
| pDAB113029 | 24 | 0 | 0 | 173 | 81 |
| pDAB108746 | 18 | 129 | 79 | 173 | 96 |
| pDAB101556 | 2 | 0 | 0 | 131 | 125 |

TABLE 2

ELISA assay results showing cry34Ab1 and AAD-1 transgene expression in V4-6 maize roots of various construct events.

| Construct Name | No. of Events Analyzed | Mean Cry34 (ng/cm$^2$) | Cry34 STD | Mean AAD-1 (ng/cm$^2$) | AAD-1 STD |
|---|---|---|---|---|---|
| pDAB113029 | 10 | 1293 | 735 | 561 | 363 |
| pDAB108746 | 3 | 2938 | 2653 | 538 | 304 |
| pDAB101556 | 6 | 0 | 0 | 573 | 432 |

In addition, Tables 3 and 4 show T$_1$ ELISA results showing cry34Ab1 and AAD-1 transgene expression in V4-V6 maize leaves and roots, respectively, of various construct events.

TABLE 3

T$_1$ ELISA results depicting cry34Ab1 and AAD-1 transgene expression in V4-6 maize leaves.

| Construct Name | No. of samples analyzed | No. of events analyzed | Cry34Ab1 Mean (ng/mg) | Cry34 STD | AAD-1 Mean (ng/mg) | AAD-1 STD |
|---|---|---|---|---|---|---|
| pDAB101556 | 3 | 1 | 1 | 0 | 723 | 133 |
| pDAB112816 | 9 | 3 | 11 | 7 | 1043 | 308 |
| pDAB112820 | 9 | 3 | 21 | 31 | 427 | 186 |
| pDAB113029 | 9 | 3 | 7 | 10 | 1360 | 404 |

TABLE 4

T$_1$ ELISA results depicting cry34Ab1 and AAD-1 transgene expression in V4-6 maize roots.

| Construct Name | No. of samples analyzed | No. of events analyzed | Cry34Ab1 Mean (ng/mg) | Cry34 STD | AAD-1 Mean (ng/mg) | AAD-1 STD |
|---|---|---|---|---|---|---|
| pDAB101556 | 3 | 1 | 20 | 0 | 5036 | 1084 |
| pDAB112816 | 9 | 3 | 3295 | 1689 | 8040 | 1576 |
| pDAB112820 | 9 | 3 | 1683 | 1130 | 2371 | 648 |
| pDAB113029 | 9 | 3 | 4400 | 2297 | 6946 | 1971 |

As such novel *Zea mays* metallothionein-like regulatory elements were identified and characterized. Disclosed for the first time are promoter, 5'-UTR, and 3'-UTR regulatory elements for use in gene expression constructs. Various designs of the MTL promoters exhibited highly root-preferred expression compared to the leaf. Certain combinations of MTL promoter versions and their native 3' UTRs, for example pDAB112816, pDAB112820 and pDAB113029, exhibited enhancer effects on the downstream gene cassette to significantly upregulate AAD-1 expression both in leaf and roots. No such enhancer effect was observed in the control construct, pDAB101556.

Furthermore, the promoter appears to enhance the expression in multiple tissue types (e.g., leaf, root, pollen, stem, silk, cob, husk, etc.). For example, although the pDAB113029 construct MTL promoter/3' UTR does not express its own cry34Ab1 expression in various tissue types, it does enhance the expression of the downstream AAD1 cassette in multiple tissue types.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention. The following examples are provided to illustrate certain particular features and/or embodiments. The examples should not be construed to limit the disclosure to the particular features or embodiments exemplified.

What is claimed is:

1. A nucleic acid vector comprising a promoter operably linked to
   i) a polylinker sequence;
   ii) a transgene or
   iii) a combination of i) and ii),
   wherein said promoter comprises SEQ ID NO: 1 or SEQ ID NO: 2.

2. The nucleic acid vector of claim 1 wherein said promoter is less than 3 kb in length.

3. The nucleic acid vector of claim 1 wherein said promoter comprises SEQ ID NO: 1.

4. The nucleic acid vector of claim 1 wherein said promoter comprises SEQ ID NO: 2.

5. The nucleic acid vector of claim 1 wherein said promoter consists of SEQ ID NO: 1.

6. The nucleic acid vector of claim 1 wherein said promoter consists of SEQ ID NO: 2.

7. The nucleic acid vector of claim 1 further comprising a sequence encoding a selectable maker.

8. The nucleic acid vector of claim 7 wherein said promoter is operably linked to a transgene.

9. The nucleic acid vector of claim 8 wherein the transgene encodes a selectable marker or a gene product conferring insecticidal resistance, herbicide tolerance, nitrogen use efficiency, water use efficiency, or nutritional quality.

10. The nucleic acid vector of claim 1 further comprising a 3' untranslated sequence comprising SEQ ID NO: 3 or SEQ ID NO: 4,
    wherein the 3' untranslated sequence is operably linked to said polylinker or said transgene.

11. The nucleic acid vector of claim 10 wherein said 3' untranslated sequence consists of SEQ ID NO: 3.

12. The nucleic acid vector of claim 10 wherein said 3' untranslated sequence consists of SEQ ID NO: 4.

13. The nucleic acid vector of claim 1 further comprising a 5' untranslated sequence comprising SEQ ID NO: 5, wherein the 5' untranslated sequence is inserted between, and operably linked to, said promoter sequence and said polylinker or said transgene.

14. The nucleic acid vector of claim 13 wherein said 5' untranslated sequence consists of SEQ ID NO: 5.

15. A plant comprising a promoter sequence comprising SEQ ID NO: 1 or SEQ ID NO: 2, wherein the promoter is operably linked to a transgene.

16. The plant of claim 15 wherein said plant is selected from the group consisting of maize, wheat, rice, sorghum, oats, rye, bananas, sugar cane, soybean, cotton, sunflower, and canola.

17. The plant of claim 15 wherein said plant is *Zea mays*.

18. The plant of claim 15 wherein the transgene is inserted into the genome of said plant.

19. The plant of claim 15 wherein said promoter sequence comprises SEQ ID NO: 1.

20. The plant of claim 15 wherein said promoter sequence comprises SEQ ID NO: 2.

21. The plant of claim 15 wherein said promoter sequence consists of SEQ ID NO: 1.

22. The plant of claim 15 wherein said promoter sequence consists of SEQ ID NO: 2.

23. The plant of claim 15 further comprising a 5' untranslated sequence comprising SEQ ID NO: 5, wherein the 5' untranslated sequence is inserted between, and operably linked to, said promoter and said transgene.

24. The plant of claim 23 further comprising a 3' untranslated sequence comprising SEQ ID NO: 3 or SEQ ID NO: 4,
    wherein the 3' untranslated sequence is operably linked to said transgene.

25. The plant of claim 24 wherein said 3' untranslated sequence comprises SEQ ID NO: 3.

26. The plant of claim 24 wherein said 3' untranslated sequence comprises SEQ ID NO: 4.

27. The plant of claim 24 wherein said 3' untranslated sequence consists of SEQ ID NO: 3.

28. The plant of claim 24 wherein said 3' untranslated sequence consists of SEQ ID NO: 4.

* * * * *

SEQUENCE LISTING

```
<160> NUMBER OF SEQ ID NOS: 15

<210> SEQ ID NO 1
<211> LENGTH: 2061
<212> TYPE: DNA
<213> ORGANISM: Zea mays

<400> SEQUENCE: 1
accatatcat gtctcaagcc ttaatacact tttaaataaa tttaaatcat ttaatagaaa      60
ctaattacat gttaatacat cactataaaa aaaattaatg gttgcaccgt aaagctttaa     120
cttgtgcatc tatactctaa tagtttgtgg tccaacgcct cggtccgaca tctatagaag     180
tctttttttc tttattattt ggtttctttg tgagcttcac gttcagtttg gccctatttg     240
tactcttgca tatacttata gatatgtaac atgttttcta acatcttgct tgagatgtta     300
ttcattcgaa gcatcccttt gtctaagtcc acttgtgcac cctttgaaaa aatgttagca     360
taaatgattg tgttaaccat caaaacacca aaactttatt ttaaacggac ctaagtctat     420
tttacttgca atgagctagc atgaggaaca tggagcaaca ttaaactcga aacaggaggc     480
agtatcaaat actccctctg tttcttttta ttagtcgctg gatagtgaaa ttttgcacta     540
tccagcgact aataaaaaga aacggaggga gtatgagagt cgatcttaag aacatgacgt     600
atgatccata ccctcaaatc tgtttgagaa aaatcactat cgaaggaggc tacttgtttt     660
cttctttgcg tagaagataa tactcctcct gtcctaaatt aatatttgtt taaacttttt     720
actaaattca tgtaataatt aatgtatgcg ttatatatat atgtctaggt ttataattat     780
tcatatgaat atgaacataa aaatctaggg ctaaaacgac tactattttg aaaacggaag     840
gagtagtaag ttatttaagc ggaggggaac catgatgggc tagtgattta atttacatat     900
atatattggt gttctgggct cttacatgag aagatctagt taactgttgt tactgaacag     960
cgaagacaaa tatataattt aagctcccca actgctagtg attctgttaa gaggtaatgt    1020
ttaaagtaaa tttacaagag cccgtctagc tcagtcggta gagcgcaagg ctcttaacct    1080
tgtggtcgtg ggttcgagcc ccacggtggg cgcacaattt tttgtttttt gacatttttt    1140
gtttgcttag ttgcagacgg ttttccccct gctaggagat ttccgagaga aaaaaaaggc    1200
actacaggtt aaccaaaacc accaacctttt ggagcgtcga ggcgacgggc atttgcgtag    1260
ttgaagctta caaagttgca tatgagatga gtgccggaca tgaagcggat aacgttttaa    1320
actggcaaca atatctagct gtttcaaatt caggcgtggg aagctacgcc tacgcgccct    1380
ggacggcgtg taaagagcca gcatcggcat cattgtcaaa cgatcgacaa ggccaagaaa    1440
```

```
ttccaaatat attattaata aaaaagaagg cacaaattag tttggttttt tagtatgtgt    1500
ggcggaggaa attttgagaa cgaacgtatc aagaaggca caagacgata tagattgacg      1560
cggctagaag ttgcagcaag acagtgggta cggtcttata tatcctaata aataaaaaat     1620
aaaactatag tgtgtcaaat gtcaacaaga ggaggaggca gccaaattag cagagggaga    1680
caagtagagc acgccttatt agcttgctta tttatcgtgg tggtgtactt gttaattact    1740
ggcacgcatt atcaacaacg cagttctgga tgtgaatcta gacaaacatt tgtctaggtt    1800
ccgcacgtat agttttttt  ctttttttt  tgggggggg  gtggggggg  ggggaacgg     1860 aagctgtaat aaacggtact aggaacgaaa gcaaccgccg cgcgcatgtt tttgcaatag    1920
attacggtga ccttgatgca ccaccgcgtg ctataaaaac cagtgtcccc gagtctactc    1980
atcaaccaat ccataactcg aaaccttttc ttgtgctctg ttctgtctgt gtgtttccaa    2040
agcaaacgaa agaggtcgag g                                              2061

<210> SEQ ID NO 2
<211> LENGTH: 1498
<212> TYPE: DNA
<213> ORGANISM: Zea mays

<400> SEQUENCE: 2
tttaacttgt gcatctatac tctaatagtt tgtggtccaa cgcctcggtc cgacatctat      60
agaagtcttt ttttctttat tatttggttt ctttgtgagc ttcacgttca gtttggccct     120
atttgtactc ttgcatatac ttatagatat gtaacatgtt ttctaacatc ttgcttgaga     180
tgttattcat tcgaagcatc cctttgtcta agtccacttg tgcaccctt  gagctagcat     240 gaggaacatg gagcaacatt aaactcgaaa caggaggcag tatcaaatga gagtcgatct     300
taagaacatg acgtatgatc catacacctca aatctgtttg agaaaaatca ctatcgaagg    360
aggctacttg ttttcttctt tgcgtagaag ataagtaagt tatttaagcg aggggaacc      420 atgatgggct agtgatttaa tttacatata tatattggtg ttctgggctc ttacatgaga     480
agatctagtt aactgttgtt actgaacagc gaagacaaat atataatta  agctccccaa     540 ctgctagtga ttctgttaag aggtaatgtt taaagtaaat tgcttagttg cagacggttt    600
ttcccctgct aggagatttc cgagagaaaa aaaggcact  acaggttaac caaaaccacc    660
aacctttgga gcgtcgaggc gacgggcatt tgcgtagttg aagcttacaa agttgcatat    720
gagatgagtg ccggacatga agcggataac gtttaaact  ggcaacaata tctagctgtt   780
tcaaattcag gcgtgggaag ctacgcctac gcgccctgga cggcgtgtaa agagccagca    840
tcggcatcat tgtcaaacga tcgacaaggc caagaaattc caaatatatt attaataaaa    900
aagaaggcac aaattagttt ggtttttag tatgtgtggc ggaggaaatt ttgagaacga     960
acgtatcaaa gaaggcacaa gacgatatag attgacgcgg ctagaagttg cagcaagaca    1020
gtgggtacgg tcttatata  cctaataaat aaaaataaa  actatagtgt gtcaaatgtc    1080
aacaagagga ggaggcagcc aaattagcag agggagacaa gtagagcacg ccttattagc    1140
ttgcttattt atcgtggtgg tgtacttgtt aattactggc acgcattatc aacaacgcag    1200
ttctggatgt gaatctagac aaacattgt  ctaggttccg cacgtatagt ttttttctt     1260 ttttttttgg ggggggggtg gggggggg   ggaacggaag ctgtaataaa cggtactagg    1320
aacgaaagca accgccgcgc gcatgttttt gcaatagatt acggtgacct tgatgcacca    1380
ccgcgtgcta taaaaccag  tgtccccgag tctactcatc aaccaatcca taactcgaaa    1440
```

```
cctttcttg tgctctgttc tgtctgtgtg tttccaaagc aaacgaaaga ggtcgagg    1498

<210> SEQ ID NO 3
<211> LENGTH: 1080
<212> TYPE: DNA
<213> ORGANISM: Zea mays

<400> SEQUENCE: 3
tcctgctgcg ttgtttcgtt tgcggcatgc atggatgtca ccttttttt  actgtctgct      60 ttgtgcttgt ggcgtgtcaa gaataaagga tggagccatc gtctggtctg actctggctc    120
tccgccatgc atgcttggtg tcggttctgt tgtgcttgtg ttggtgcatg taatcgtatg    180
gcatcgttac acaccatgca tctctgatct ctttgcgcca gtgtgtgtga ctatgtccct    240
gtaacgattg gctcagtgat tgaatatata tacaatactg ttttactaag taagtatgat    300
tacctcttat tttaaatttc tctatgtaaa tcatgtcttc tacacagtat gttgtacgac    360
cactatctgc tgaatgtata gatgtctaga aagcacgtgg cccgttagca tgacacgaag    420
cacggttttt tagcacgaca caaattaaca tgggcccagg ctcagcccgg ccagcgagc     480 gtgtcgggct cgacagccat cccgacgcgt tgggctggcc cgagcacggc ccggtggatg    540
ttgggcttag aaaccggccc gctacatttt agcgcagcct aacccactgc ccaccaatac    600
tccgcaattc cgcataaatc ccccagtgcc ccatccccag cccattgacc agcgcgacag    660
ctagggctgg aaaaaaagct cgaggctcgc gagccagctc gggctcgatc aggctcggct    720
cggctcggtg aggctcgcga gcctaaacga gcccgagccg agcctaattc cgcagctcgc    780
tacactaacg agccgagccg gcttggtgag gctcgcgagc gggctcaagg cttggtccaa    840
actactactt actcgtatct ccgttcacca gtgtgtaagt gtgctgtttt ggtcacaact    900
cacaaggaac tagagtgcag ggacataatt ttttattata tggaacatat tgtgcttcaa    960
atttgagcta atgactataa ttattgttgt tgagtacttg agtgtacagg ctcgcgagcc   1020
tatatcgagc cgagcctcat taccgagctc gctaagtgac cgagccgagc ctggctcggc   1080

<210> SEQ ID NO 4
<211> LENGTH: 376
<212> TYPE: DNA
<213> ORGANISM: Zea mays

<400> SEQUENCE: 4
tcctgctgcg ttgtttcgtt tgcggcatgc atggatgtca ccttttttt  actgtctgct      60 ttgtgcttgt ggcgtgtcaa gaataaagga tggagccatc gtctggtctg actctggctc    120
tccgccatgc atgcttggtg tcggttctgt tgtgcttgtg ttggtgcatg taatcgtatg    180
gcatcgttac acaccatgca tctctgatct ctttgcgcca gtgtgtgtga ctatgtccct    240
gtaacgattg gctcagtgat tgaatatata tacaatactg ttttactaag taagtatgat    300
tacctcttat tttaaatttc tctatgtaaa tcatgtcttc tacacagtat gttgtacgac    360
cactatctgc tgaatg                                                    376

<210> SEQ ID NO 5
<211> LENGTH: 81
<212> TYPE: DNA
<213> ORGANISM: Zea mays

<400> SEQUENCE: 5
atcaaccaat ccataactcg aaacctttc ttgtgctctg ttctgtctgt gtgtttccaa     60
agcaaacgaa agaggtcgag g                                              81
```

<210> SEQ ID NO 6
<211> LENGTH: 3496
<212> TYPE: DNA
<213> ORGANISM: Zea mays

<400> SEQUENCE: 6

| | | | | | |
|---|---|---|---|---|---|
| accatatcat | gtctcaagcc | ttaatacact | tttaaataaa | tttaaatcat | ttaatagaaa | 60 |
| ctaattacat | gttaatacat | cactataaaa | aaaattaatg | gttgcaccgt | aaagctttaa | 120 |
| cttgtgcatc | tatactctaa | tagtttgtgg | tccaacgcct | cggtccgaca | tctatagaag | 180 |
| tcttttttc | tttattattt | ggtttctttg | tgagcttcac | gttcagtttg | gccctatttg | 240 |
| tactcttgca | tatacttata | gatatgtaac | atgttttcta | acatcttgct | tgagatgtta | 300 |
| ttcattcgaa | gcatcccttt | gtctaagtcc | acttgtgcac | cctttgaaaa | aatgttagca | 360 |
| taaatgattg | tgttaaccat | caaaacacca | aaactttatt | ttaaacggac | ctaagtctat | 420 |
| tttacttgca | atgagctagc | atgaggaaca | tggagcaaca | ttaaactcga | aacaggaggc | 480 |
| agtatcaaat | actccctctg | tttcttttta | ttagtcgctg | gatagtgaaa | ttttgcacta | 540 |
| tccagcgact | aataaaaaga | aacggaggga | gtatgagagt | cgatcttaag | aacatgacgt | 600 |
| atgatccata | ccctcaaatc | tgtttgagaa | aaatcactat | cgaaggaggc | tacttgtttt | 660 |
| cttctttgcg | tagaagataa | tactcctcct | gtcctaaatt | aatatttgtt | taaactttt | 720 |
| actaaattca | tgtaataatt | aatgtatgcg | ttatatatat | atgtctaggt | ttataattat | 780 |
| tcatatgaat | atgaacataa | aaatctaggg | ctaaaacgac | tactattttg | aaaacggaag | 840 |
| gagtagtaag | ttatttaagc | ggaggggaac | catgatgggc | tagtgattta | atttacatat | 900 |
| atatattggt | gttctgggct | cttacatgag | aagatctagt | taactgttgt | tactgaacag | 960 |
| cgaagacaaa | tatataattt | aagctccca | actgctagtg | attctgttaa | gaggtaatgt | 1020 |
| ttaaagtaaa | tttacaagag | cccgtctagc | tcagtcggta | gagcgcaagg | ctcttaacct | 1080 |
| tgtggtcgtg | ggttcgagcc | ccacggtggg | cgcacaattt | tttgttttt | gacatttttt | 1140 |
| gtttgcttag | ttgcagacgg | ttttccct | gctaggagat | ttccgagaga | aaaaaaaggc | 1200 |
| actacaggtt | aaccaaaacc | accaaccttt | ggagcgtcga | ggcgacgggc | atttgcgtag | 1260 |
| ttgaagctta | caaagttgca | tatgagatga | gtgccggaca | tgaagcggat | aacgttttaa | 1320 |
| actggcaaca | atatctagct | gttttcaaatt | caggcgtggg | aagctacgcc | tacgcgccct | 1380 |
| ggacggcgtg | taaagagcca | gcatcggcat | cattgtcaaa | cgatcgacaa | ggccaagaaa | 1440 |
| ttccaaatat | attattaata | aaaagaagg | cacaaattag | tttggttttt | tagtatgtgt | 1500 |
| ggcggaggaa | attttgagaa | cgaacgtatc | aaagaaggca | caagacgata | tagattgacg | 1560 |
| cggctagaag | ttgcagcaag | acagtgggta | cggtcttata | tatcctaata | aataaaaaat | 1620 |
| aaaactatag | tgtgtcaaat | gtcaacaaga | ggaggaggca | gccaaattag | cagagggaga | 1680 |
| caagtagagc | acgccttatt | agcttgctta | tttatcgtgg | tggtgtactt | gttaattact | 1740 |
| ggcacgcatt | atcaacaacg | cagttctgga | tgtgaatcta | gacaaacatt | tgtctaggtt | 1800 |
| ccgcacgtat | agttttttt | ctttttttt | tgggggggg | gtgggggggg | ggggaacgg | 1860 |
| aagctgtaat | aaacggtact | aggaacgaaa | gcaaccgccg | cgcgcatgtt | tttgcaatag | 1920 |
| attacggtga | ccttgatgca | ccaccgcgtg | ctataaaaac | cagtgtcccc | gagtctactc | 1980 |
| atcaaccaat | ccataactcg | aaaccttttc | ttgtgctctg | ttctgtctgt | gtgtttccaa | 2040 |
| agcaaacgaa | agaggtcgag | gatgtcttgc | agctgcggat | caagctgcaa | ctgcggatca | 2100 |

-continued

```
agctgcaagt gcgggtaatg taattaaggc tcttattttc ctttctgtaa ctgtgtgatc    2160
gtgtcctttt gtgaattgta cgtggtgtct tttttttaa ttttttttt tttgcttaat     2220 tctgcgcagc aagatgtacc ctgacctgga ggagaagagc ggcggggggcg ctcaggccag   2280 cgccgccgcc gtcgtcctcg gcgttgcccc tgagacgaag aaggcggcgc agttcgaggc   2340
ggcgggcgag tccggcgagg ccgctcacgg ctgcagctgc ggtgacagct gcaagtgcag   2400 ccctgcaac tgctgatcct gctgcgttgt ttcgtttgcg gcatgcatgg atgtcacctt    2460
ttttttactg tctgctttgt gcttgtggcg tgtcaagaat aaaggatgga gccatcgtct   2520
ggtctgactc tggctctccg ccatgcatgc ttggtgtcgg ttctgttgtg cttgtgttgg   2580
tgcatgtaat cgtatggcat cgttacacac catgcatctc tgatctcttt gcgccagtgt   2640
gtgtgactat gtccctgtaa cgattggctc agtgattgaa tatatataca atactgtttt   2700
actaagtaag tatgattacc tcttatttta aatttctcta tgtaaatcat gtcttctaca   2760
cagtatgttg tacgaccact atctgctgaa tgtatagatg tctagaaagc acgtggcccg   2820
ttagcatgac acgaagcacg gttttttagc acgacacaaa ttaacatggg cccaggctca   2880
gcccggccca gcgagcgtgt cgggctcgac agccatcccg acgcgttggg ctggcccgag   2940
cacggcccgg tggatgttgg gctttagaaac cggcccgcta cattttagcg cagcctaacc   3000
cactgcccac caatactccg caattccgca taaatccccc agtgccccat ccccagccca   3060
ttgaccagcg cgacagctag ggctggaaaa aaagctcgag gctcgcgagc cagctcgggc   3120
tcgatcaggc tcggctcggc tcggtgaggc tcgcgagcct aaacgagccc gagccgagcc   3180
taattccgca gctcgctaca ctaacgagcc gagccggctt ggtgaggctc gcgagcgggc   3240
tcaaggcttg gtccaaacta ctacttactc gtatctccgt tcaccagtgt gtaagtgtgc   3300
tgttttggtc acaactcaca aggaactaga gtgcagggac ataatttttt attatatgga   3360
acatattgtg cttcaaattt gagctaatga ctataattat tgttgttgag tacttgagtg   3420
tacaggctcg cgagcctata tcgagccgag cctcattacc gagctcgcta agtgaccgag   3480
ccgagcctgg ctcggc                                                   3496
```

```
<210> SEQ ID NO 7
<211> LENGTH: 17
<212> TYPE: DNA
<213> ORGANISM: Artificial Sequence
<220> FEATURE:
<223> OTHER INFORMATION: nucleotide primer

<400> SEQUENCE: 7
gccataccct ccagttg                                                   17

<210> SEQ ID NO 8
<211> LENGTH: 23
<212> TYPE: DNA
<213> ORGANISM: Artificial Sequence
<220> FEATURE:
<223> OTHER INFORMATION: nucleotide primer

<400> SEQUENCE: 8
gccgttgatg gagtagtaga tgg                                            23

<210> SEQ ID NO 9
<211> LENGTH: 18
<212> TYPE: DNA
<213> ORGANISM: Artificial Sequence
<220> FEATURE:
<223> OTHER INFORMATION: nucleotide primer
```

<400> SEQUENCE: 9
ccgaatccaa cggcttca                                                    18

<210> SEQ ID NO 10
<211> LENGTH: 18
<212> TYPE: DNA
<213> ORGANISM: Artificial Sequence
<220> FEATURE:
<223> OTHER INFORMATION: nucleotide primer

<400> SEQUENCE: 10
tggcggacga cgacttgt                                                    18

<210> SEQ ID NO 11
<211> LENGTH: 19
<212> TYPE: DNA
<213> ORGANISM: Artificial Sequence
<220> FEATURE:
<223> OTHER INFORMATION: nucleotide primer

<400> SEQUENCE: 11
aaagtttgga ggctgccgt                                                   19

<210> SEQ ID NO 12
<211> LENGTH: 21
<212> TYPE: DNA
<213> ORGANISM: Artificial Sequence
<220> FEATURE:
<223> OTHER INFORMATION: nucleotide primer

<400> SEQUENCE: 12
cgagcagacc gccgtgtact t                                                21

<210> SEQ ID NO 13
<211> LENGTH: 20
<212> TYPE: DNA
<213> ORGANISM: Artificial Sequence
<220> FEATURE:
<223> OTHER INFORMATION: nucleotide primer

<400> SEQUENCE: 13
tgttcggttc cctctaccaa                                                  20

<210> SEQ ID NO 14
<211> LENGTH: 22
<212> TYPE: DNA
<213> ORGANISM: Artificial Sequence
<220> FEATURE:
<223> OTHER INFORMATION: nucleotide primer

<400> SEQUENCE: 14
caacatccat caccttgact ga                                               22

<210> SEQ ID NO 15
<211> LENGTH: 24
<212> TYPE: DNA
<213> ORGANISM: Artificial Sequence
<220> FEATURE:
<223> OTHER INFORMATION: nucleotide primer

<400> SEQUENCE: 15
cacagaaccg tcgcttcagc aaca                                             24